(12) United States Patent
Armani et al.

(10) Patent No.: US 7,968,724 B2
(45) Date of Patent: Jun. 28, 2011

(54) ESTER DERIVATIVES AS PHOSPHODIESTERASE INHIBITORS

(75) Inventors: Elisabetta Armani, Parma (IT); Gabriele Amari, Parma (IT); Gino Villetti, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 171 days.

(21) Appl. No.: 12/334,621

(22) Filed: Dec. 15, 2008

(65) Prior Publication Data

US 2009/0170903 A1     Jul. 2, 2009

(30) Foreign Application Priority Data

Dec. 14, 2007   (EP) .................................... 07024322

(51) Int. Cl.
C07D 405/00 (2006.01)
A01N 43/40 (2006.01)

(52) U.S. Cl. ..................................... 546/284.1; 514/337

(58) Field of Classification Search ............... 546/284.1; 514/337
See application file for complete search history.

(56) References Cited

U.S. PATENT DOCUMENTS

2008/0015226 A1   1/2008  Amari et al.

FOREIGN PATENT DOCUMENTS

| WO | 94-02465 | 2/1994 |
| WO | 95-35281 | 12/1995 |
| WO | 2006-064355 | 6/2006 |

OTHER PUBLICATIONS

Buist, A. S., "Similarities and Differences between Asthma and Chronic Obstructive Pulmonary Disease: Treatment and Early Outcomes", Eur. Respir. J. 2003; 21: Suppl. 39, pp. 30s-35s.*
U.S. Appl. No. 12/188,631, filed Aug. 8, 2008, Delcanale, et al.
Jacobitz, S. et al., *Molecular Pharmacology.*, 1996, 50, 891-899.
Giembycz, M.A. et al., *Expert Opin. Investg. Drugs.*, 2001; 10:1361-1379.
U.S. Appl. No. 12/700,926, filed Feb. 5, 2010, Amari, et al.

* cited by examiner

*Primary Examiner* — Janet L Andres
*Assistant Examiner* — Heidi Reese
(74) *Attorney, Agent, or Firm* — Oblon, Spivak, McClelland, Maier & Neustadt, L.L.P.

(57) ABSTRACT

The invention provides inhibitors of the phosphodiesterase 4 (PDE4) enzyme. More particularly, the invention relates to compounds that are new ester derivatives, methods of preparing such compounds, compositions containing them, and therapeutic uses thereof.

42 Claims, No Drawings

ESTER DERIVATIVES AS PHOSPHODIESTERASE INHIBITORS

CROSS REFERENCES TO RELATED APPLICATIONS

This application claims priority to European Patent Application No. 07024322.5, filed on Dec. 14, 2007, which is incorporated herein by reference in its entirety.

BACKGROUND OF THE INVENTION

1. Field of the Invention

The present invention relates to inhibitors of the phosphodiesterase 4 (PDE4) enzyme. More particularly, the present invention relates to compounds that are new ester derivatives, methods of preparing such compounds, compositions containing such compounds, and therapeutic uses of such compounds.

2. Discussion of the Background

Airway obstruction characterizes a number of sever respiratory diseases including asthma and chronic obstructive pulmonary disease (COPD). Events leading to airway obstruction include oedema of airway walls, increased mucous production and inflammation.

Drugs for treating respiratory diseases such as asthma and COPD are currently administered through inhalation. One of the advantages of the inhalatory route over the systemic one is the possibility of delivering the drug directly at the site of action, avoiding any systemic side-effects, thus resulting in a more rapid clinical response and a higher therapeutic ratio.

Inhaled corticosteroids are the current maintenance therapy of choice for asthma and together with bronchodilator beta2-agonists for acute symptom relief, they form the mainstay of current therapy for the disease. The current management of COPD is largely symptomatic by means of bronchodilating therapy with inhaled anticholinergics and inhaled beta2-adrenoceptor agonists. However, corticosteroids do not reduce the inflammatory response in COPD as they do in asthma.

Another class of therapeutic agents which has been widely investigated in view of its anti-inflammatory effects for the treatment of inflammatory respiratory diseases such as asthma and COPD is represented by the inhibitors of the enzymes phosphodiesterases (PDEs), in particular of the phosphodiesterase type 4 (hereinafter referred to as PDE4).

Various compounds acting as PDE4 inhibitors have been disclosed in the prior art. However, the usefulness of several PDE4 inhibitors of the first-generation such as rolipram and piclamilast has been limited due to their undesirable side effects. Said effects include nausea and emesis due to their action on PDE4 in the central nervous system and gastric acid secretion due to the action on PDE4 in parietal cells in the gut.

The cause of said side effects has been widely investigated.

It has been reported that PDE4 exists in two distinct forms representing different conformations, that were designated as high affinity rolipram binding site or HPDE4, especially present in the central nervous system and in parietal cells, and low affinity rolipram binding site or LPDE4 (see, Jacobitz, S et al., *Mol. Pharmacol.*, 1996, 50, 891-899), which is found in the immune and inflammatory cells. While both forms appear to exhibit catalytic activity, they differ with respect to their sensitivity to inhibitors. In particular, compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as cilomilast and roflumilast. However, even these compounds are not provided with a good selectivity towards LPDE4.

In fact, according to the literature (Giembycz M A et al., *Expert Opin. Investg. Drugs,* 2001; 10:1361-1379) cilomilast has an affinity toward HPDE4 comparable to that toward LPDE4, after oral administration (HPDE4 $IC_{50}$=120 nM; LPDE4 $IC_{50}$=90 nM; HPDE4/LPDE4 ratio about 1.3).

Other classes of compounds acting as PDE4 inhibitors have been disclosed in the prior art. For example, WO 9402465 discloses, among others, ketone derivatives of general formula

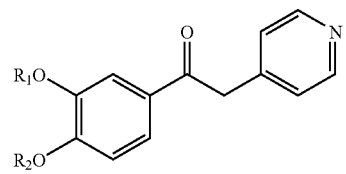

wherein $R_1$ is lower alkyl and $R_2$ may be alkyl, alkenyl, cycloalkyl, cycloalkyl, cycloalkenyl, cyclothioalkyl or cyclothioalkenyl.

WO 95/35281 concerns tri-substituted phenyl derivatives generically belonging to the classes of ethers and enolethers.

WO 2006/064355 concerns heterocyclic compounds useful for the treatment of inflammatory and allergic disorders.

Although several PDE4 inhibitors have been disclosed so far, there is still a need for more efficacious and better tolerated compounds. In particular it would be highly advantageous to provide more selective compounds, e.g. endowed with a higher affinity toward the LPDE4 in comparison to HPDE4, in order to attenuate or avoid the side effects associated with its inhibition.

SUMMARY OF THE INVENTION

Accordingly, it is one object of the present invention to provide novel PDE4 inhibitors.

It is another object of the present invention to provide novel PDE4 inhibitors which exhibit a higher affinity toward the LPDE4 in comparison to HPDE4.

It is another object of the present invention to provide novel methods of preparing such a PDE4 inhibitor.

It is another object of the present invention to provide novel pharmaceutical compositions which contain such a PDE4 inhibitor.

It is another object of the present invention to provide novel methods of treating certain diseases and conditions by administering such a PDE4 inhibitor.

These and other objects, which will become apparent during the following detailed description, have been achieved by the inventors' discovery that ester derivatives of general formula (I)

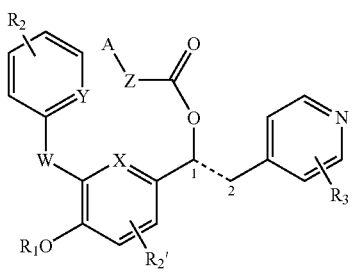

(I)

wherein:
the broken line between atoms 1 and 2 stands for a single or a double bond;
X and Y may be carbon atoms substituted with a hydrogen atom or $R_2'$ and $R_2$, respectively, or carbon atoms which are linked by a single bond;
W is selected from the group consisting of O, $S(O)_m$ wherein m=0, 1 or 2, and $NR_4$, wherein $R_4$ is H, $C_1$-$C_6$ alkyl; $C_2$-$C_6$ alkenyl or $C_2$-$C_6$ alkynyl;
Z is selected from the group consisting of
  $(CH_2)_n$ wherein n=0, 1 or 2;
  $(CH_2)_pO$ wherein p=1, 2 or 3;
  $O(CH_2)_q$ wherein q=0, 1, 2 or 3;
  $CH_2SO_2$;
  $CH_2NR_4$;
  $NR_5$ wherein $R_5$ is H or $C_1$-$C_6$ alkyl and
  $CR_6R_7$ wherein
    $R_6$ is independently selected from H or $C_1$-$C_6$ alkyl, preferably methyl and
    $R_7$ is independently selected from the group consisting of
      $C_1$-$C_6$ alkyl, preferably methyl;
      phenyl;
      benzyl;
      $NH_2$;
      HNCOOR', wherein R' is $C_1$-$C_6$ alkyl, preferably t-butyl;
    or when $R_6$ and $R_7$ are both alkyl they together with the carbon atom to which they are linked form a ring having 3, 4, 5, or 6 carbon atoms, preferably having 3 carbon atoms;
$R_1$ is selected from the group consisting of
  H;
  $C_1$-$C_6$ alkyl, optionally substituted by one or more substituents selected from the group consisting of $C_3$-$C_7$ cycloalkyl and $C_3$-$C_7$ cycloalkenyl;
  $C_3$-$C_7$ cycloalkyl;
  $C_5$-$C_7$ cycloalkenyl;
  $C_2$-$C_6$ alkenyl, and
  $C_2$-$C_6$ alkynyl;
when X and Y are not linked by a single bond, there may be one, two, three, four, or five $R_2$ substituents and there may be one, two, or three $R_2'$ substituents, and when X and Y are linked by a single bond, there may be one, two, three, or four $R_2$ substituents and there may be one or two $R_2'$ substituents, and each $R_2$ and $R_2'$ is independently one or more groups selected from the group consisting of
  H;
  $C_1$-$C_6$ alkyl, optionally substituted by one or more substituents selected from the group consisting of $C_3$-$C_7$ cycloalkyl and $C_3$-$C_7$ cycloalkenyl;
  $C_3$-$C_7$ cycloalkyl;
  $C_3$-$C_7$ cycloalkenyl;
  $C_2$-$C_6$ alkenyl;
  $C_2$-$C_6$ alkynyl;
  halogen atoms;
  cyano;
  nitro;
  $NR_8R_9$ wherein $R_8$ and $R_9$ are different or the same and are independently selected from the group consisting of
    H;
    $C_1$-$C_6$ alkyl, optionally substituted with phenyl;
    $COC_6H_5$;
    $COC_1$-$C_4$ alkyl;
    or together with the nitrogen atom to which they are linked they form a saturated or partially saturated ring, preferably a piperidyl ring;
  $OR_{10}$ or $COR_{10}$ wherein $R_{10}$ is phenyl, $C_1$-$C_6$ alkyl, $C_1$-$C_6$ alkynyl, or $C_1$-$C_6$ alkenyl;
  oxo;
  $HNSO_2R_{11}$ wherein $R_{11}$ is $C_1$-$C_6$ alkyl or a phenyl optionally substituted with halogen atoms or with a $C_1$-$C_6$ alkyl group;
  $SO_2R_{12}$ wherein $R_{12}$ is $C_1$-$C_6$ alkyl, OH, or $NR_8R_9$ wherein $R_8$ and $R_9$ are as defined above;
  $SOR_{13}$ wherein $R_{13}$ is phenyl, or $C_1$-$C_6$ alkyl;
  $SR_{14}$ wherein $R_{14}$ is H, phenyl, or $C_1$-$C_6$ alkyl;
  $COOR_{15}$ wherein $R_{15}$ is H, $C_1$-$C_6$ alkyl, phenyl, benzyl; and
  $(CH_2)_rOR_{16}$, wherein r=1, 2, 3 or 4 and $R_{16}$ is H or $C_1$-$C_6$ cycloalkyl;
there may be one, two, three, or four $R_3$ substituents and each $R_3$ is independently selected from the group consisting of H, cyano, nitro, $CF_3$, and halogen atoms, preferably chlorine;
A is an optionally substituted ring system in which the optional substituent, $R_x$, consists of one or more groups, which may be the same or different, and are independently selected from the group consisting of:
  $C_1$-$C_6$ alkyl optionally substituted by one or more $C_3$-$C_7$ cycloalkyl;
  $C_2$-$C_6$ alkenyl optionally substituted by one or more $C_3$-$C_7$ cycloalkyl;
  $C_2$-$C_6$ alkynyl optionally substituted by one or more $C_3$-$C_7$ cycloalkyl;
  $C_3$-$C_7$ cycloalkyl;
  $C_3$-$C_7$ cycloalkenyl;
  $OR_{17}$ wherein $R_{17}$ is selected from the group consisting of
    H;
    $C_1$-$C_6$ alkyl optionally substituted by one or more $C_3$-$C_7$ cycloalkyl;
    $C_3$-$C_7$ cycloalkyl;
    phenyl;
    benzyl;
    $C_1$-$C_6$ alkyl-$NR_{18}R_{19}$ wherein $R_{18}$ and $R_{19}$ are independently selected from the group consisting of H and $C_1$-$C_6$ alkyl or together with the nitrogen atom to which they are linked form a saturated or partially saturated ring, preferably a piperidyl ring;
  halogen atoms;
  cyano;
  nitro;
  $NR_8R_9$ wherein $R_8$ and $R_9$ are as defined above;
  $OR_{10}$ or $COR_{10}$ wherein $R_{10}$ is as defined above
  oxo;
  $HNSO_2R_{11}$ wherein $R_{11}$ is $C_1$-$C_6$ alkyl or a phenyl optionally substituted with halogen atoms or with a $C_1$-$C_6$ alkyl group;
  $SO_2R_{12}$ wherein $R_{12}$ is $C_1$-$C_6$ alkyl, OH, or $NR_8R_9$ wherein $R_8$ and $R_9$ are as defined above;
  $SOR_{13}$ wherein $R_{13}$ is phenyl or $C_1$-$C_6$ alkyl;

SR$_{14}$ wherein R$_{14}$ is H, phenyl, or C$_1$-C$_6$ alkyl;

COOR$_{15}$ wherein R$_{15}$ is H, C$_1$-C$_6$ alkyl, phenyl, benzyl; and (CH$_2$)$_r$OR$_{16}$, wherein r=1, 2, 3 or 4 and R$_{16}$ is H or C$_1$-C$_6$ cycloalkyl are useful as PDE4 inhibitors.

The invention also includes pharmaceutically acceptable salts of compounds of general formula (I) and the corresponding N-oxides on the pyridine ring.

The present invention also provides pharmaceutical compositions of compounds of general formula (I) or pharmaceutically acceptable salts thereof or pyridine ring N-oxides thereof alone or in combination with other therapeutic active ingredients including those currently used in the treatment of respiratory disorders, e.g. beta2-agonists, corticosteroids and anticholinergic or antimuscarinic agents and/or in admixture with one or more pharmaceutically acceptable carriers.

The present invention also provides the use of compounds of general formula (I) for preparing a medicament.

In a further aspect the present invention provides the use of compounds of general formula (I) for the preparation of a medicament for the prevention and/or treatment of an inflammatory disease, disorder or condition characterized by or associated with an undesirable inflammatory immune response or induced by or associated with an excessive secretion of TNF-α and PDE4.

Moreover the present invention provides methods for the prevention and/or treatment of an inflammatory disease, disorder or condition characterized by or associated with an undesirable inflammatory immune response or induced by or associated with an excessive secretion of TNF-α and PDE4 which comprises administering to a subject in need thereof a therapeutically effective amount of a compound of general formula (I) or a pharmaceutically acceptable salt there of or a pyridine ring N-oxide thereof.

For the treatment of an inflammatory disease, disorder or condition characterized by or associated with an undesirable inflammatory immune response or induced by or associated with an excessive secretion of TNF-α and PDE4, the compounds according to the invention are preferably administered by inhalation.

Inhalable preparations include inhalable powders, propellant-containing metering aerosols or propellant-free inhalable formulations. Therefore the invention is also directed to a device which may be a single- or multi-dose dry powder inhaler, a metered dose inhaler and a soft mist nebulizer comprising one or more compounds of general formula (I) or a pharmaceutically acceptable salt thereof or a pyridine ring N-oxide thereof.

The invention further comprises a process for the preparation of compounds of general formula (IIA) and (IIB):

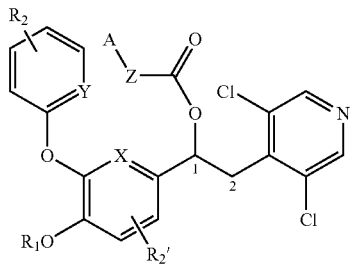

(IIA)

wherein X, Y, R$_1$, R$_2$, R$_2$', Z and A are as defined above;

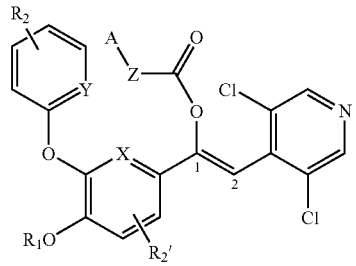

(IIB)

wherein X, Y, R$_1$, R$_2$, R$_2$' and A are as defined above.

The PDE4 inhibitors of the present invention are efficaciously active upon inhalation administration and are characterized by a short systemic duration and hence they may be endowed with less side effects associated to the systemic activity of the drugs.

DETAILED DESCRIPTION OF THE PREFERRED EMBODIMENTS

The term "halogen atoms" as used herein includes fluorine, chlorine, bromine, and iodine, preferably chlorine.

As used herein, the expression "C$_1$-C$_x$ alkyl" where x is an integer greater than 1, refers to straight-chained and branched alkyl groups wherein the number of constituent carbon atoms is in the range 1 to x. Particular alkyl groups are methyl, ethyl, n-propyl, isopropyl and t-butyl. Optionally, in said groups one or more hydrogen atoms can be replaced by halogen atoms, preferably chlorine or fluorine. The derived expressions "C$_2$-C$_x$ alkenyl" and "C$_2$-C$_x$ alkynyl", are to be construed in an analogous manner.

As used herein, the expression "C$_3$-C$_x$ cycloalkyl", where x is an integer greater than 3, refers to cyclic non-aromatic hydrocarbon groups containing from 3 to x ring carbon atoms. Examples include cyclopropyl, cyclobutyl, cyclopentyl, cyclohexyl, and cycloheptyl. Optionally in said groups one or more hydrogen atoms can be replaced by halogen atoms, preferably chlorine or fluorine. The derived expression "C$_3$-C$_x$ cycloalkenyl", where x is an integer greater than 5, is to be construed in an analogous manner.

As used herein, the expression "ring system" refers to mono-, bi-, or tricyclic ring systems which may be saturated, partially unsaturated, or unsaturated, such as aryl, C$_3$-C$_8$ cycloalkyl, or heteroaryl, having 5 to 10 ring atoms in which at least 1 ring atom is a hereoatom (e.g. N, S or O). Examples of suitable monocyclic systems include phenyl, pyridyl, piperazinyl, piperidinyl, morpholinyl, cyclopentyl, cyclohexyl, cyclohexenyl, and cycloheptyl. Examples of suitable bicyclic systems include naphthyl, quinolinyl, isoquinolinyl, indenyl and the partially- or fully-hydrogenated derivatives thereof. Examples of suitable tricyclic systems include dibenzofuran, dibenzothiophene, and dibenzopyrrole.

The invention is directed to compounds believed to act as inhibitors of the phosphodiesterase 4 (PDE4) enzyme. Said class of compounds inhibit the conversion of cyclic nucleotides, in particular cyclic adenosine monophosphate (cAMP), into their inactive 5'-mononucleotide forms.

In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-1, IL-3, and tumor necrosis factor—alpha (TNF-α).

In particular the present invention relates to compounds belonging to general formula (I) described above. The invention also includes the pharmaceutically acceptable salts thereof and the corresponding N-oxides on the pyridine ring.

Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which acidic functions, when present, are reacted with an appropriate base to form, e.g. sodium, potassium, calcium, magnesium, and ammonium salts.

Most of the compounds of the prior art are provided with a moiety capable of interacting with the sub-pockets $S_0$ and $S_1$ of the hydrophobic region such as a substituted cathecol group and with another moiety capable of indirectly interacting with the metal ions of the $S_2$ sub-pocket, for example a heterocycle such as pyridine or pyrrolidone.

The present invention is directed to compounds which are believed to interact with the sub-pockets $S_0$ and $S_1$ by means of the substituted catecol moiety and the interaction with the metal ions region by means of the pyridine ring like other known PDE4 inhibitors but differ by the presence of a further group able of establishing an additional interaction with the sub-pocket $S_3$.

It will be apparent to those skilled in the art that the compounds of general formula (I) may contain asymmetric centers. Therefore the invention also includes the optical stereoisomers and mixtures thereof.

When there are less than four $R_3$ substituents, they may be bonded in any of the possible sites on the ring to which $R_3$ is bonded. For example, when there is only one $R_3$ substituent, it may be ortho or meta to the nitrogen atom in the ring to which $R_3$ is bonded. When there are two $R_3$ substituents, they may be both ortho, both meta, or one ortho and one meta (either ortho or para to each other) to the nitrogen atom in the ring to which $R_3$ is bonded. When there are three $R_3$ substituents, they may be bonded to all but one ortho position or all but one meta relative to the nitrogen atom in the ring to which $R_3$ is bonded.

Similarly, when there are less than the maximum $R_2$ and $R_2'$ substituents, they may also be bonded in any of the possible sites on the rings to which they are bonded.

It will also be apparent to those skilled in the art that the compounds of general formula (I), when the broken line between atoms 1 and 2 is a double bond, can exhibit geometrical isomerism. Therefore the invention includes both the E- and Z geometric isomers on the double bond (cis and trans forms). Preferably the substituents on the double bond in compounds of general formula (I) are arranged in the trans conformation (Z-isomers).

The compounds of general formula (I) were found to show an in vitro inhibitory activity toward the PDE4 enzyme in nM concentrations. They also give rise to no significant detectable plasma levels which is, in turn, an indication of supposed short systemic action.

A preferred group of compounds of general formula (I) is that wherein W is an oxygen atom and the pyridine ring is substituted in 3 and 5 with two atoms of chlorine, according to the general formula (II):

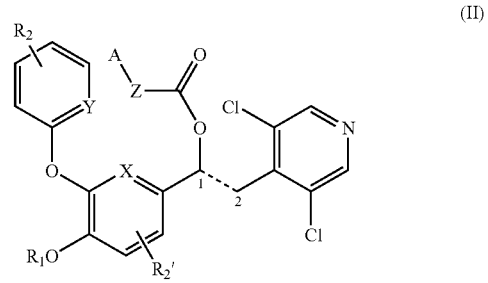

(II)

A preferred group of compounds of general formula (II) is that wherein the broken line between 1 and 2 is a single bond, according to the general formula (IIA):

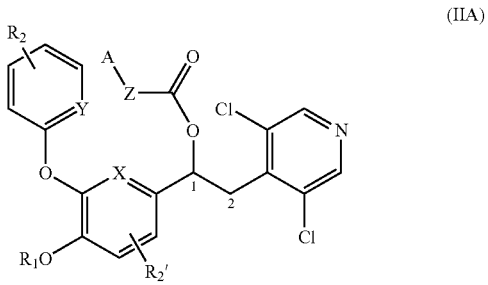

(IIA)

wherein X, Y, $R_1$, $R_2$, $R_2'$, Z and A are as defined above.

A first group of compounds of general formula (IIA) is represented by the compounds belonging to the general formula (IIA'), wherein X and Y are carbon atoms substituted with a hydrogen atom:

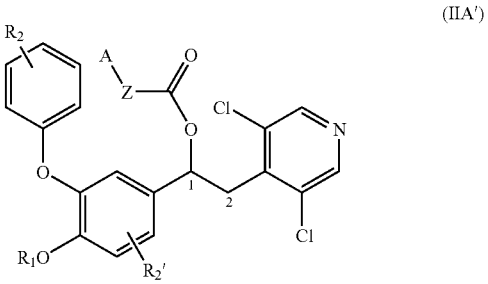

(IIA')

wherein $R_1$, $R_2$, $R_2'$, Z and A are as defined above.

A first group of more preferred compounds of general formula (IIA') is that in which:

$R_1$, $R_2$ and $R_2'$ are as defined above;

Z is $(CH_2)_n$ wherein n is 0; and

A is as defined above.

A second group of more preferred compounds of general formula (IIA') is that in which:

$R_1$, $R_2$ and $R_2'$ are as defined above;

Z is $CHR_6$ wherein $R_6$ is $C_1$-$C_6$ alkyl, preferably methyl; and

A is as defined above.

A third group of more preferred compounds of general formula (IIA') is that in which:

$R_1$, $R_2$ and $R_2'$ are as defined above;

Z is $CR_5R_6$ wherein $R_5$ and $R_6$ are both $C_1$-$C_6$ alkyl and together with the carbon atom to which they are linked they form a ring having 3, 4, 5 or 6 carbon atoms, preferably having 3 carbon atoms; and A is as defined above.

A second group of compounds of general formula (IIA) is represented by the following general formula (IIA") wherein X and Y are linked by a single bond:

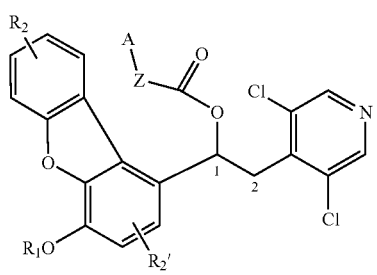

(IIA")

wherein $R_1$, $R_2$, $R_2'$, Z and A are as defined above.

A first group of more preferred compounds of general formula (IIA") is that in which:

$R_1$, $R_2$, $R_2'$ are as defined above; preferably methyl, $NO_2$ and hydrogen;

Z is $(CH_2)_n$ wherein n is 0; and

A is as defined above.

A second group of more preferred compounds of general formula (IIA") is that in which:

$R_1$ and $R_2$ are as defined above;

Z is $CHR_6$ wherein $R_7$ is $C_1$-$C_6$ alkyl, preferably methyl; and

A is as defined above.

A third group of more preferred compounds of general formula (IIA") is that in which:

$R_1$, $R_2$, $R_2'$ are as defined above;

Z is $CR_6R_7$ wherein $R_6$ and $R_7$ are both $C_1$-$C_6$ alkyl and they form a ring with the carbon atom to which they are linked having 3, 4, 5 or 6 carbon atoms, preferably having 3 carbon atoms; and A is as defined above.

Another preferred group of compounds of general formula (II) is that wherein the broken line between 1 and 2 is a double bond, represented by the following general formula (IIB):

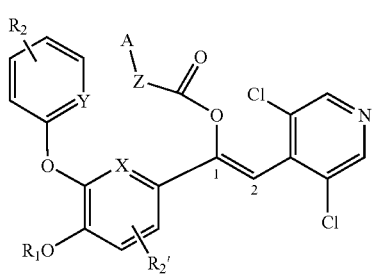

(IIB)

wherein X, Y, $R_1$, $R_2$, $R_2'$ and A are as defined above.

A first group of compounds of general formula (IIB) is represented by the following general formula (IIB'), in which X and Y are carbon atoms substituted with a hydrogen atom:

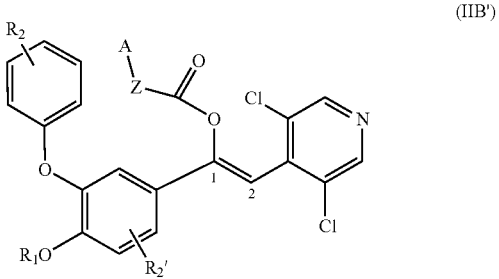

(IIB')

wherein $R_1$, $R_2$, $R_2'$, Z and A are as defined above.

A first group of more preferred compounds of general formula (IIB') is that in which:

$R_1$, $R_2$, $R_2'$ are as defined above;

Z is $(CH_2)_n$ wherein n is 0; and

A is as defined above.

A second group of more preferred compounds of general formula (IIB') is that in which:

$R_1$, $R_2$, $R_2'$ are as defined above;

Z is $CHR_7$ wherein $R_7$ is $C_1$-$C_6$ alkyl, preferably methyl; and

A is as defined above.

A third group of more preferred compounds of general formula (IIB') is that in which:

$R_1$, $R_2$, $R_2'$ are as defined above;

Z is $CR_6R_7$ wherein $R_6$ and $R_7$ are both $C_1$-$C_6$ alkyl and they form a ring with the carbon atom to which they are linked having 3, 4, 5 or 6 carbon atoms, preferably having 3 carbon atoms; and A is as defined above.

A second group of compounds of general formula (IIB) is represented by the following general formula (IIB"), wherein X and Y are linked by a single bond:

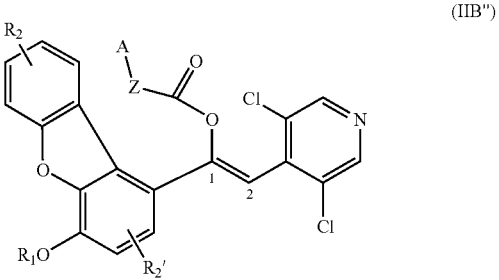

(IIB")

wherein $R_1$, $R_2$, $R_2'$, Z and A are as defined above.

A first group of more preferred compounds of general formula (IIB") is that in which:

$R_1$, $R_2$, $R_2'$ are as defined above; preferably methyl, $NO_2$ and hydrogen;

Z is $(CH_2)_n$ wherein n is 0; and

A is as defined above.

A second group of preferred compounds of general formula (IIB") is that in which:

$R_1$, $R_2$, $R_2'$ are as defined above;

Z is $CHR_7$ wherein $R_7$ is $C_1$-$C_6$ alkyl, preferably methyl; and

A is as defined above.

A third group of more preferred compounds of general formula (IIB") is that in which:

$R_1$, $R_2$ and $R_2'$ are as defined above;

Z is $CR_6R_7$ wherein $R_6$ and $R_7$ are both $C_1$-$C_6$ alkyl and they form a ring with the carbon atom to which they are linked having 3, 4, 5 or 6 carbon atoms, preferably having 3 carbon atoms; and A is as defined above.

In one of the preferred embodiment the optional substituent Rx of the ring system A is selected from the group consisting of $C_1$-$C_6$ alkyl, $C_2$-$C_6$ alkenyl, $C_2$-$C_6$ alkynyl or $OR_{17}$ wherein $R_{17}$ is as defined above.

In another preferred embodiment $R_x$ is a group able of improving the aqueous solubility of the whole molecule such as $NR_8R_9$ or $HNSO_2R_{11}$ wherein $R_8$, $R_9$ and $R_{11}$ are as defined above.

In a particular embodiment, when X and Y are linked by a single bond, $R_1$ is preferably $C_1$-$C_6$ alkyl, $R_2$ is preferably selected from the group consisting of H, $NH_2$, $NO_2$, more preferably $NH_2$ or $NO_2$ and $R_2'$ is preferably hydrogen.

In another particular embodiment of the invention, when the ring system A is a heteroaryl ring, the ring is preferably selected from the group consisting of pyrrole, pyrazole, furan, thiophene, imidazole, oxazole, isoxazole, thiazole, pyridine, pyrimidine, pyrazine and pyran.

In a further aspect the present invention provides the preferred compounds listed in Table 1:

Advantageously the compounds of the invention are characterized by a selectivity toward LPDE4 higher than that toward HPDE4 as obtained by the determination of their $IC_{50}$. In the case of LPDE4, the $IC_{50}$ is the molar concentration of the test compound producing 50% inhibition of cAMP disappearance, assessed as described in Cortijo J et al., *Br. J. Pharmacol.*, 1993, 108: 562-568, while in the case of HPDE4, the $IC_{50}$ is the molar concentration of the test compound producing 50% inhibition of the binding of [$H^3$] rolipram, assessed as described in Duplantier A J et al., *J. Med. Chem.*, 1996; 39: 120-125. Preferably the HPDE4/LPDE $IC_{50}$ ratio for the compounds of the invention is higher than 10, more preferably higher than 100, even more preferably higher than 300.

The compounds of general formula (I) may be prepared according to conventional methods known to the person skilled in the art. Some of the processes which can be used are described below and reported in Scheme 1 and should not be viewed as limiting the scope of the synthetic methods available for the preparation of the compounds of the invention.

TABLE 1

| Compound | Chemical name |
|---|---|
| 1 | Benzoic acid 2-(3,5-dichloro-pyridin-4-yl)-1-(4-methoxy-8-nitro-dibenzofuran-1-yl)-vinyl ester |
| 2 | Benzoic acid 2-(3,5-dichloro-pyridin-4-yl)-1-(4-methoxy-dibenzofuran-1-yl)-vinyl ester |
| 3 | (S)-2-(4-Isobutyl-phenyl)-propionic acid 2-(3,5-dichloro-pyridin-4-yl)-1-(4-methoxy-8-nitro-dibenzofuran-1-yl)-vinyl ester |
| 4 | Benzoic acid 2-(3,5-dichloro-pyridin-4-yl)-1-(4-methoxy-8-amino-dibenzofuran-1-yl)-vinyl ester |
| 5 | Benzoic acid 2-(3,5-dichloro-pyridin-4-yl)-1-(8-methanesulfonylamino-4-methoxy-dibenzofuran-1-yl)-vinyl ester |
| 6 | Benzoic acid 2-(3,5-dichloro-1-oxy-pyridin-4-yl)-1-(4-methoxy-8-nitro-dibenzofuran-1-yl)-vinyl ester |
| 7 | Benzoic acid 2-(3,5-dichloro-1-oxy-pyridin-4-yl)-1-(4-methoxy-dibenzofuran-1-yl)-vinyl ester |
| 8 | Benzoic acid 1-(4-methoxy-8-methanesulphonylamino-dibenzofuran-1-yl)-2-(1-oxy-3,5-dichloro-pyridin-4-yl)-vinyl ester |
| 9 | Benzoic acid 2-(3,5-dichloro-pyridin-4-yl)-1-(4-methoxy-8-nitro-dibenzofuran-1-yl)-ethyl ester |
| 10 | Benzoic acid 2-(3,5-dichloro-pyridin-4-yl)-1-(4-methoxy-dibenzofuran-1-yl)ethyl ester |
| 11 | 3-Cyclopropylmethoxy-4-difluoromethoxy benzoic acid 2-(3,5-dichloro-pyridin-4-yl)-1-[4-methoxy-3-(4-nitro-phenoxy)-phenyl]-ethyl ester |
| 12 | Benzoic acid 1-(4-methoxy-8-nitro-dibenzofuran-1-yl)-2-(1-oxy-3,5-dichloro-pyridin-4-yl)-ethyl ester |
| 13 | Benzoic acid 1-(4-methoxy-dibenzofuran-1-yl)-2-(1-oxy-3,5-dichloro-pyridin-4-yl)-ethyl ester |
| 14 | 3-Cyclopropylmethoxy-4-difluoromethoxy-benzoic acid 2-(3,5-dichloro-1-oxy-pyridin-4-yl)-1-[4-methoxy-3-(4-nitro-phenoxy)-phenyl]-ethyl ester |
| 15 | Benzoic acid 1-(3-chloro-4-methoxy-dibenzofuran-1-yl)-2-(3,5-dichloro-1-oxy-pyridin-4-yl)-ethyl ester |
| 16 | 2-(4-Isobutyl-phenyl)-propionic acid 2-(3,5-dichloro-pyridin-4-yl)-1-(4-methoxy-8-nitro-dibenzofuran-1-yl)-ethyl ester) |
| 17 | 4-Methoxy-8-nitro-dibenzofuran-1-carboxilic acid 2-(3,5-dichloro-pyridin-4-yl)-1-(4-methoxy-8-nitro-dibenzofuran-1-yl)-vinyl ester |
| 18 | 4-(2-Piperidin-1-yl-ethoxy)-benzoic acid 2-(3,5-dichloro-1-oxy-pyridin-4-yl)-1-(4-methoxy-dibenzofuran-1-yl)-ethyl ester |
| 19 | 3-Cyclopropylmethoxy-4-difluoromethoxy-benzoic acid 2-(3,5-dichloro-1-oxy-pyridin-4-yl)-1-(4-methoxy-8-nitro-dibenzofuran-1-yl)-ethyl ester |

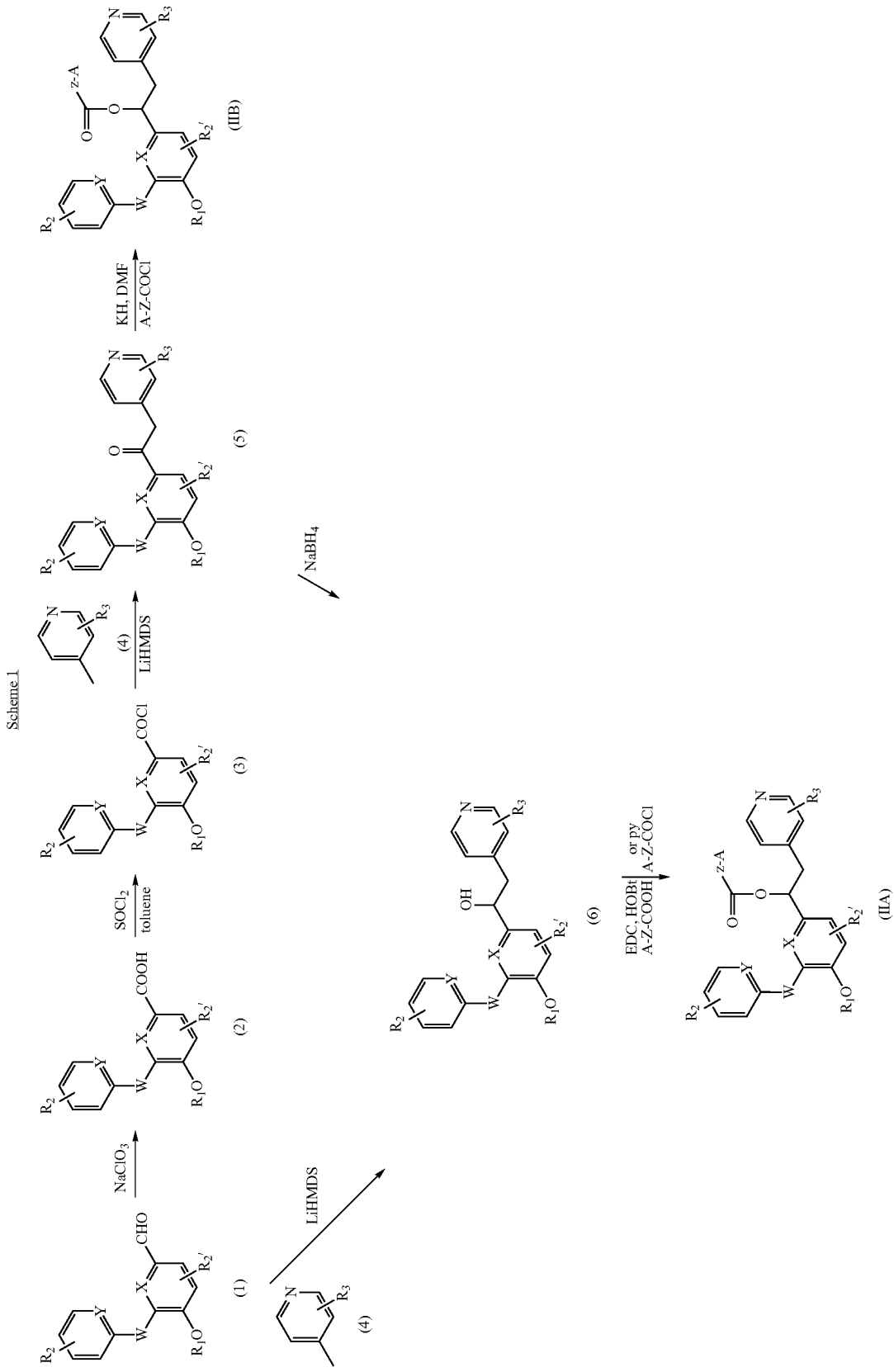
Scheme 1

Preparation of compounds of formula (IIA) in which 1 and 2 form a single bond.

According to a particular embodiment of the present invention, the compounds of general formula (IIA) may be prepared according to a process which includes the following steps:

$1^{st}$ step—Reducing an ethanone derivative of general formula (5) to give an alcohol derivative of general formula (6).

The reaction may be carried out by using sodium boron hydride ($NaBH_4$) in a solvent such as methanol at room temperature under nitrogen atmosphere.

$2^{nd}$ step—Adding a suitable acid of formula AZCOOH to a solution of the alcohol derivative of general formula (6) to give a compound of general formula (IIA).

The reaction is carried out in the presence of a suitable strong base such as lithium diisopropylamide (LDA), NaH, dimethylaminopyridine (DMAP) and in the presence of a condensing agent such as 1-Ethyl-3-[3-dimethylaminopropyl]carbodiimide hydrochloride (EDC) and N-hydroxybenzotriazole (HOBT) in a solvent such as dichloromethane under nitrogen atmosphere. Other solvents may be used, such as dimethylformamide (DMF), tetrahydrofuran (THF), chloroform, dioxane and any other aprotic solvent known to those skilled in the art. In a particular embodiment, the reaction may also be carried out in absence of solvents.

Compounds of general formula (IIA) may be also prepared by adding a suitable acyl chloride of general formula A-Z—COCl or a suitable isocyanate of general formula A-Z—NCO to a solution of the alcohol derivative of general formula (6), with a suitable base in a stoichiometric or a catalytic amount, according to procedures well known to the skilled person.

The alcohol derivative of general formula (6) may alternatively be prepared by reacting a benzaldheyde derivative of formula (1) with a methylpyridine derivative of formula (4) using lithium-bis-(trimethylsilyl)-amide (LiHMDS) or similar strong bases and a solvent such as tetrahydrofuran (THF) or other aprotic solvents.

Intermediates of general formula (1) and (4) are commercially available or may be prepared according to methods available in the literature and well known to the person skilled in the art.

Preparation of compounds of formula (IIB) in which 1 and 2 form a double bond.

These compounds may be prepared according to a process which includes the following steps:

$1^{st}$ step—reaction of an acyl chloride of formula (3) wherein $R_1$ and $R_2$ are as defined above with a 4-methylpyridine of formula (4) wherein $R_3$ is as defined above to give an ethanone derivative of general formula (5).

The reaction may be carried out by activation of the methyl group of a compound of formula (4) by means of an equimolar amount of a strong base such as NaH, lithium diisopropylamide (LDA), dimethylaminopyridine (DMAP) in an aprotic solvent such as tetrahydrofurane (THF) dimethylformamide (DMF), ethyl ether, dioxane, or toluene at a temperature comprised between −80° and −20° C. and subsequent addition of an acyl chloride, also maintained at a temperature comprised between −80° to −20° C., preferably between −80° and −60° C.

The medium reaction is maintained at the temperature comprised between −80° and −20° C., preferably between −80° and −60° C., and quenched with water maintained at the same temperature to obtain the ethanone of formula (5).

The compounds of formula (3) are commercially available. The compounds of formula (4) are commercially available or may be prepared according to any suitable method known to the person skilled in the art. For example, the preparation of the 3,5-dichloro-4-methylpyridine is reported in WO 94/14742.

$2^{nd}$ step—isolation of the obtained ethanone by means of conventional procedure known to the person skilled in the art such as filtration.

$3^{rd}$ step—reaction of the ethanone of step 2) with a strong base such as NaH, KH, LDA, DMAP in an aprotic solvent such as THF, DMF, ethyl ether, dioxane, toluene at a temperature comprised between −80° and −20° C. to obtain the corresponding reactive enolate, followed by addition of a suitable acyl chloride AZCOCl or a suitable isociante ANCO or $ACH_2NCO$ in a equimolar ratio or in a slight excess, wherein A and Z are as defined above, at a temperature comprised between −80° and room temperature, to obtain the final product.

The aldehyde derivatives of formula (1) in which X and Y are carbons linked by a single bond may be prepared according to the following Scheme 2.

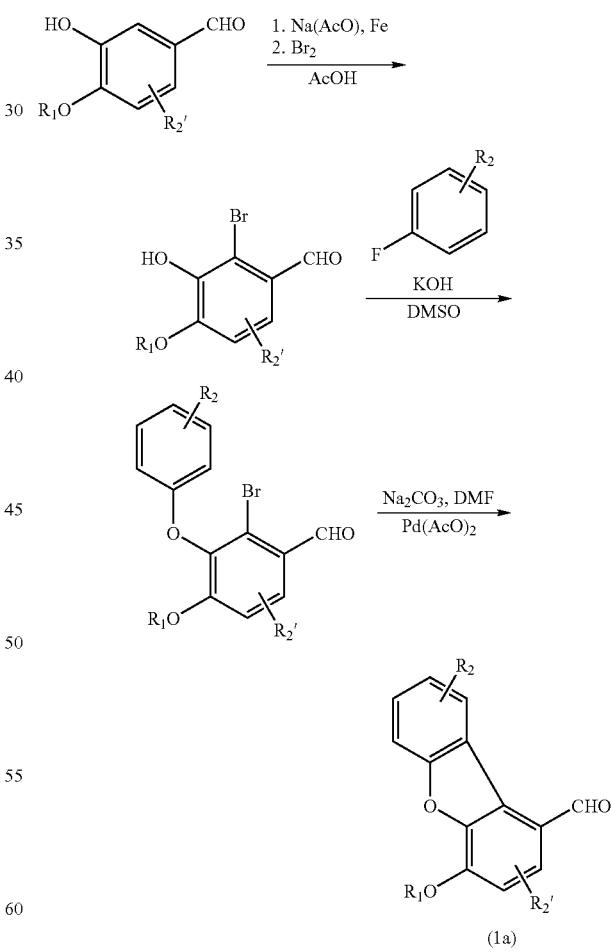

Scheme 2 Preparation of 4-alkoxy-8-nitro-dibenzofuran-1-carbaldehyde derivatives The aldehyde derivatives of formula (1) in which X and Y are carbon atoms substituted with a hydrogen atom may be prepared according to the following Scheme 3.

Scheme 3 Preparation of 4-alkoxy-3-(4-nitro-phenoxy)-benzaldehyde

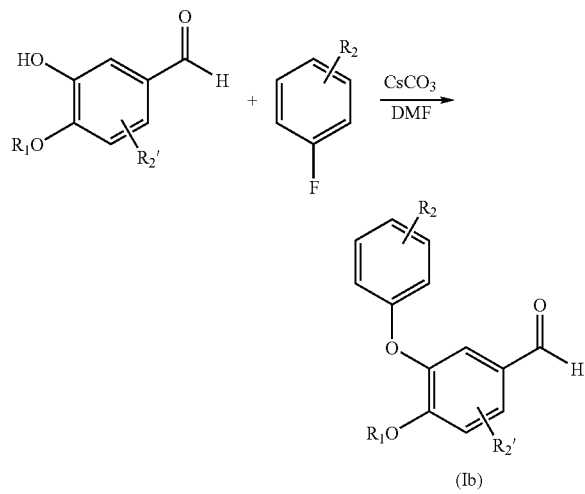

Compounds (5) may be prepared starting from the aldehydes of general formula (1).

In particular aldheyde 1(a) may be prepared starting from 3-hydroxy-4-alkyloxybenzaldehydes by bromination with a brominating agent to give the 2-bromo derivatives that can be transformed into 2-bromo-3-(4-nitrophenyloxy)-4-alkyloxy-benzaldehydes, by condensation with 4-fluoro-nitrobenzene under basic conditions, and these may be cyclized with a catalyst such as palladium diacetate (Scheme 2).

Aldheydes of formula 1(b) may be prepared starting from 3-hydroxy-4-alkyloxybenzaldehydes by condensation with 4-fluoro-nitrobenzene under basic conditions (Scheme 3).

From aldehydes (1), by oxidation with sodium chloride in a solvent such as dioxane/water under acidic conditions, carboxylic acids (2) are obtained. These may be transformed into the corresponding acyl chlorides (3) by means of thienyl chloride in an aprotic solvent such as toluene under reflux and condensed with 4-methylpyridines (4) previously treated with a strong base such as lithium-hexamethyldisililazide (LiHMDS) in an aprotic solvent such as THF, giving ketones (enols) (5).

The N-oxides on the 2-pyridinyl ring may be prepared according to methods available in the literature and well known to the skilled person. For instance they may be prepared by dissolving the compound of general formula (IIB) in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

For those compounds in which the ring system A is a ring substituted with a functional group sensitive to oxidation, the corresponding N-oxides are alternatively prepared by carrying out the oxidation step before the $2^{nd}$ step.

The present invention also provides pharmaceutical compositions of compounds of general formula (I) in admixture with one or more pharmaceutically acceptable carriers, for example those described in Remington's Pharmaceutical Sciences Handbook, XVII Ed., Mack Pub., N.Y., U.S.A.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized, wherein the powder can be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction can be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination with other pharmaceutical active ingredients including those currently used in the treatment of respiratory disorders, e.g. beta2-agonists, corticosteroids and anticholinergic or antimuscarinic agents.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of general formula (I), pharmaceutically acceptable salts thereof, and pyridine ring N-oxides thereof can be administered for example, at a dosage of 0.001 to 1000 mg/day, preferably between 0.1 to 500 mg/day.

When they are administered by inhalation route, the dosage of the compounds of general formula (I), pharmaceutically acceptable salts thereof, and pyridine ring N-oxides thereof is advantageously 0.1 to 40 mg/day, preferably 0.2 to 30 mg/day.

Preferably, the compounds of general formula (I), pharmaceutically acceptable salts thereof, and pyridine ring N-oxides thereof alone or combined with other active ingredients may be administered for the prevention and/or treatment of an inflammatory disease, disorder or condition characterized by or associated with an undesirable inflammatory immune response or induced by or associated with an excessive secretion of TNF-α and PDE4.

However the compounds of general formula (I), pharmaceutically acceptable salts thereof, and pyridine ring N-oxides thereof may be administered for the prevention and/or treatment of any disease induced by or associated with an excessive secretion of TNF-α and PDE4, such as allergic conditions and autoimmune diseases. Said disease include: allergic disease states such as atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritis in the anogenital area, alopecia greata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases, and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Administration may be accomplished according to patient needs, for example, orally, nasally, parenterally (subcutaneously, intravenously, intramuscularly), intratracheally or by inhalation. The preferred route of administration is by inhalation.

Other features of the invention will become apparent in the course of the following descriptions of exemplary embodiments which are given for illustration of the invention and are not intended to be limiting thereof.

EXAMPLES

Example 1

Preparation of 4-Methoxy-8-nitro-dibenzofuran-1-carbaldehyde (1a) (According to Scheme 2)

Step 1. Preparation of 2-Bromo-3-hydroxy-4-methoxy-benzaldehyde

3-Hydroxy-4-methoxy-benzaldehyde (20.0 g, 131.4 mmoles) and sodium acetate (23.7 g, 289.2 mmoles) are suspended in acetic acid (650 mL). Iron powder (513.8 mg, 9.2 mmoles) is added and the resulting suspension is cooled to approximately 15° C. A solution of bromine (23.1 g, 144.6 mmoles) in acetic acid (130 mL) is slowly (over 1 hour) dropped into the reaction mixture, keeping temperature at approximately 15° C. The reaction is left at room temperature for 30 minutes. The crude is poured in 780 mL of brine; the desired compound is filtered-off from the mother liquor and washed, sequentially, with brine and water. The product is dried under vacuum overnight to afford a white solid (26.6 g), which is used in the next step without further purification.

| $R_1$ | $R_2'$ | analytical |
|---|---|---|
| Me | H | MS/ESI⁺230.9, 232.9 [MH]⁺ |

Step 2. Preparation of 2-Bromo-4-methoxy-3-(4-nitro-phenoxy)-benzaldehyde

2-Bromo-3-hydroxy-4-methoxy-benzaldehyde (15.0 g, 64.9 mmoles) is dissolved in DMSO (100 mL). Potassium hydroxide (4.01 g, 71.4 mmoles) and 1-Fluoro-4-nitro-benzene (13.74 g, 97.4 mmoles) are added to the solution. The reaction mixture is stirred at 130° C. for 3 hours. As the crude is poured in water (500 mL), precipitation occurs. The solid is filtered, washed with water and dried under vacuum overnight. The pale-brown solid obtained (23.4 g) is used in the next step without further purification.

| $R_1$ | $R_2'$ | $R_2$ | analytical |
|---|---|---|---|
| Me | H | NO₂ | MS/ESI⁺351.9, 353.8 [MH]⁺ |

Step 3. Preparation of 4-Methoxy-8-nitro-dibenzofuran-1-carbaldehyde (1a)

2-Bromo-4-methoxy-3-(4-nitro-phenoxy)-benzaldehyde (19.4 g, 55.1 mmoles) is dissolved in dry DMF (450 mL) under nitrogen atmosphere. Sodium carbonate (7.0 g, 66.11 mmoles) and palladium acetate (1.15 g, 5.1 mmoles) are added to the solution. The reaction mixture is heated at 130° C. for 18 hours. The crude is filtered and the mother liquor is poured in water. Precipitation occurs. The suspended solid is filtered, washed with water and dried under vacuum overnight to afford a pale brown solid (8.8 g).

| $R_1$ | $R_2$ | $R_2'$ | analytical |
|---|---|---|---|
| Me | $NO_2$ | H | MS/ESI$^+$ 272.2 [MH]$^+$ |

Example 2

Preparation of
4-methoxy-dibenzofuran-1-carbaldehyde (According to Scheme 2)

Step 1. Preparation of 4-hydroxy-dibenzofuran 4-dibenzofuran boronic acid (4.02 g, 18.9 mmoles) is suspended in diethyl ether (50 mL). The suspension is cooled to 0° C. and hydrogen peroxide (30% in $H_2O$) is added dropwise; the resulting mixture is heated to reflux for 1.5 hours to complete conversion of the starting material. The reaction mixture is then cooled to 0° C. and 1N HCl (4 mL) is added. The organic layer is washed with an aqueous solution containing 10% $FeCl_2$, dried over $Na_2SO_4$ and evaporated to dryness to give 3.48 g of the desired compound which is employed in the next step without further purification.

MS/ESI$^+$185.1 [MH]$^+$

Step 2. Preparation of 4-methoxy-dibenzofuran 4-hydroxy-dibenzofuran (5.19 g, 28.2 mmoles) is dissolved in acetone (175 mL) under nitrogen atmosphere. Solid $K_2CO_3$ (5.85 g, 42.3 mmoles) and iodomethane (7.9 mL, 126.9 mmoles) are added and the resulting mixture is vigorously stirred to reflux (40° C.) to complete conversion of the starting material (7h). The reaction mixture is evaporated to dryness, the crude is then dissolved in water and extracted with DCM; the combined organic layers are washed again with water and brine, dried over sodium sulphate and evaporated to dryness to give the desired product as a white solid (5.48 g) which is employed in the next step without further purification.

MS/ESI$^+$199.2 [MH]$^+$

Step 3. Preparation of 4-methoxy-dibenzofuran-1-carbaldehyde 4-methoxy-dibenzofuran (3.07 g, 15.5 mmoles) is dissolved in DCM (50 mL) under nitrogen atmosphere. The solution is cooled to 0° C. and dichloromethyl-methyl ether (1.68 mL, 18.6 mmoles) and subsequently $TiCl_4$ (1N solution in DCM, 18.6 mL, 18.6 mmoles) are added dropwise. The solution is stirred at 0° C. and the reaction is completed after 1 hour. The reaction mixture is poured into cold water and extracted with DCM. The combined organic layers are washed again with water and brine, dried over sodium sulphate and evaporated to dryness to give 3.54 g of crude compound. The reaction is repeated on additional 2.04 g of starting material to yield additional 2.51 g of crude compound. The two crude mixtures are combined and purified together by flash chromatography on $SiO_2$ (eluent: gradient AcOEt/hexane from 10/90 to 20/80) to give 3.8 g of the desired compound.

| $R_1$ | $R_2$ | $R_2'$ | analytical |
|---|---|---|---|
| Me | H | H | MS/ESI$^+$ 227.13 [MH]$^+$;<br>$^1$H NMR (300 MHz, CDCl$_3$) δ ppm 10.25 (s, 1H), 9.01 (ddd, 1H), 7.86 (d, 1H), 7.64-7.72 (m, 1H), 7.53-7.63 (m, 1H), 7.45 (ddd, 1H), 7.14 (d, 1H), 4.18 (s, 3H) |

Example 3

Preparation of
4-Methoxy-3-(4-nitro-phenoxy)-benzaldehyde (According to Scheme 3)

4-Methoxy-3-hydroxy-benzaldehyde (1.0 mg, 7.5 mmoles) is dissolved in DMF (20 mL). Cesium carbonate (2.45 g, 7.5 mmoles) and 1-fluoro-4-nitro-benzene (1.75 mL, 7.5 mmoles) are added and the resulting mixture is stirred at room temperature for 20 hours. The reaction mixture is then quenched by addition of 1N HCl and extracted with AcOEt. The organic layer is dried over $Na_2SO_4$ and the solvent is evaporated. The crude mixture is purified by chromatography on $SiO_2$ (eluent:hexane:AcOEt=9:1) to yield 2.0 g of the pure title compound.

| $R_1$ | $R_2$ | $R_2'$ | analytical |
|---|---|---|---|
| Me | $NO_2$ | H | MS/ESI$^+$ 273.0 [MH]$^+$ |

Example 4

Preparation of
4-methoxy-8-nitro-dibenzofuran-1-carboxylic acid (2a) (According to Scheme 1)

4-Methoxy-8-nitro-dibenzofuran-1-carbaldehyde (1.03 g, 3.8 mmoles) is suspended in a mixture of dioxane (60 mL) and water (10 mL). Sodium chloride (0.445 g, 4.93 mmoles) and sulphamic acid (2.09 g, 21.6 mmoles) are added and the mixture is stirred at room temperature for 1 hour. The mixture is then diluted with water (100 mL) and extracted with AcOEt (200 mL). The organic layer is dried over $Na_2SO_4$ and the solvent is evaporated to yield 0.701 g of raw product which is employed in the next step without further purification.

The same procedure is applied for the synthesis of 4-methoxy-dibenzofuran-1-carboxylic acid (2b), using suitable reagents.

| | $R_1$ | $R_2$ | $R_2'$ | X and Y | analytical |
|---|---|---|---|---|---|
| 2a | Me | $NO_2$ | H | Carbon atoms linked by a single bond | MS/ESI$^+$ 287.9 [MH]$^+$ |
| 2b | Me | H | H | Carbon atoms linked by a single bond | MS/ESI$^+$ 243.2 [MH]$^+$ |

Example 5

Preparation of
4-methoxy-8-nitro-dibenzofuran-1-carbonyl chloride (3a) (According to Scheme 1)

Thionyl chloride (10.5 mL, 144.2 mmoles) is added dropwise to a solution of compound (2a) (0.701 g, 2.44 mmoles)

in toluene (50 mL) and the reaction mixture is heated to reflux for 2 hours. The mixture is then evaporated to dryness under vacuum and the residue is used without further purification (0.75 g, 2.44 mmoles, 100% yield).

The same procedure is applied for the synthesis of 4-methoxy-dibenzofuran-1-carbonyl chloride (3b), using suitable reagents:

|    | $R_1$ | $R_2$ | $R_2'$ | X and Y | analytical |
|----|-------|-------|--------|---------|------------|
| 3a | Me    | $NO_2$ | H      | Carbon atoms linked by a single bond | — |
| 3b | Me    | H     | H      | Carbon atoms linked by a single bond | — |

Example 6

Preparation of 3,5-dichloro-4-methylpyridine (4) (According to Scheme 1)

Diisopropylamine (70 mL, 500 mmol) is dissolved in dry tetrahydrofuran (500 mL), the solution is cooled to −10° C. and buthyl lithium (2.5 N in hexane, 210 mL, 525 mmol) is added dropwise under stirring. After 30 minutes the solution is cooled to −20° C. and 3,5-dichloropyridine (66.6 g, 450 mmol) in tetrahydrofuran (200 mL) is added dropwise. The solution is stirred at −10° C. for 30 minutes, then cooled to −70° C. and iodomethane (50 mL, 1.6 mol) in tetrahydrofuran (100 mL) is added dropwise. The reaction mixture is allowed to warm to room temperature, quenched with water (100 mL) and extracted with diethyl ether (3×100 mL); the combined organic layers are dried over sodium sulphate (5 g) and evaporated to dryness. The crude product is crystallized twice from aqueous ethanol, then from hexane to afford 3,5-dichloro-4-methylpyridine (49.9 g, 306 mmol, 68% yield) as a white solid.

| $R_3$ | analytical |
|-------|------------|
| 3,5-Cl | MS/ESI⁺ 162.1, 164.1 [MH]⁺ |

Example 7

Preparation of 2-(3,5-Dichloro-pyridin-4-yl)-1-(4-methoxy-8-nitro-dibenzo-furan-1-yl)-ethanone (5a) (According to Scheme 1)

A solution of 3,5-dichloro-4-methyl-pyridine (0.593 g, 3.66 mmoles) in tetrahydrofuran (200 mL) is cooled to −60° C. under nitrogen atmosphere. A 1M solution of lithium bis (trimethylsilyl) amide (4.4 mL, 4.4 mmoles) is added dropwise and the resulting mixture is stirred at −60° C. for 30 minutes. A solution of 4-methoxy-8-nitro-dibenzofuran-1-carbonyl chloride (3a) (0.75 g, 2.44 mmoles) in dry tetrahydrofuran (20 mL) is added dropwise, maintaining the temperature below −60° C. After stirring for 15 minutes at −60° C., the mixture is stirred at room temperature for 3.5 hours. The mixture is then quenched with a saturated $NH_4Cl$ solution (20 mL); the product precipitated as a solid which is recovered by filtration and washed with methanol to yield 340 mg of the title compound.

The same procedure is applied for the synthesis of 2-(3,5-Dichloro-pyridin-4-yl)-1-(4-methoxy-8-dibenzo-furan-1-yl)-ethanone (5b), using suitable reagents:

|    | $R_1$ | $R_2$ | $R_2'$ | $R_3$ | X and Y | analytical |
|----|-------|-------|--------|-------|---------|------------|
| 5a | Me | $NO_2$ | H | 3,5-Cl | Carbon atoms linked by a single bond | MS/ESI⁺ 430.8, 432.8 [MH]⁺; ¹H NMR (300 MHz, CDCl₃) δ ppm 9.76 (d, 1H), 8.56 (br. s., 2H), 8.42 (dd, 1H), 8.15 (d, 1H), 7.70 (d, 1H), 7.18 (d, 1H), 4.80 (s, 2H), 4.17 (s, 3H) |
| 5b | Me | H | H | 3,5-Cl | Carbon atoms linked by a single bond | MS/ESI⁺ 430.8, 432.8 [MH]⁺; ¹H NMR (300 MHz, CDCl₃) δ ppm 8.79 (ddd, 1H), 8.58 (s, 2H), 8.08 (d, 1H), 7.66 (ddd, 1H), 7.54 (ddd, 1H), 7.36 (ddd, 1H), 7.11 (d, 1H), 4.84 (s, 2H), 4.20 (s, 3H) |

Example 8

Preparation of Benzoic Acid 2-(3,5-dichloro-pyridin-4-yl)-1-(4-methoxy-8-nitro-dibenzofuran-1-yl)-vinyl Ester (Compound 1)

Potassium hydride (KH; 35% suspension in mineral oil, 604 mg, 5.27 mmoles) and 18-crown-6 ether (1.402 g, 5.30 mmoles) are suspended in dry DMF (25 mL) under nitrogen atmosphere. The suspension is cooled to 0° C. and solid compound (5a) (1.14 g, 2.64 mmoles) is added portionwise. The resulting mixture is stirred at 0° C. for 20 minutes, then benzoyl chloride (0.97 mL, 8.35 mmoles) is added dropwise. The reaction mixture is stirred at room temperature for 24 hours, then poured into ice-cold water (30 mL); the resulting precipitate is recovered by filtration and crystallized twice from DCM to yield 1.34 g of the title compound.

The following compounds are prepared following the same route using suitable reagents:

| Cpd. | $R_1$ | $R_2$ | $R_2'$ | Z | A | $R_3$ | X and Y | analytical |
|------|-------|-------|--------|---|---|-------|---------|------------|
| 1 | Me | $NO_2$ | H | — | Ph | 3,5-Cl | Carbon atoms linked by a single bond | MS/ESI⁺ 535.18, 537.18 [MH]⁺; ¹H NMR (300 MHz, CDCl₃) δ ppm |

-continued

| Cpd. | R₁ | R₂ | R₂' | Z | A | R₃ | X and Y | analytical |
|------|----|----|----|---|---|----|---------|------------|
|      |    |    |    |   |   |    |         | 9.44 (d, 1H), 8.76 (s, 2H), 8.44 (dd, 1H), 8.01 (d, 1H), 7.87-7.94 (m, 2H), 7.73 (d, 1H), 7.58-7.67 (m, 1H), 7.40-7.49 (m, 3H), 6.95 (s, 1H), 4.08 (s, 3H) |
| 2 | Me | H | H | — | Ph | 3,5-Cl | Carbon atoms linked by a single bond | MS/ESI⁺ 490.16, 492.16 [MH]⁺; ¹H NMR (300 MHz, CDCl₃) δ ppm 8.56 (s, 2H) 8.52 (dd, 1H), 7.96 (dd, 2H), 7.65 (d, 1H), 7.61 (d, 1H), 7.51-7.58 (m, 1H), 7.44-7.51 (m, 1H), 7.30-7.44 (m, 3H), 7.06 (d, 1H), 6.58 (s, 1H), 4.12 (s, 3H) |
| 3 | Me | NO₂ | H | — | 4-I-but-Ph-Pr | 3,5-Cl | Carbon atoms linked by a single bond | MS/ESI⁺ 619.13, 621.13 [MH]⁺; ¹H NMR (300 MHz, CDCl₃) δ ppm 9.20 (d, 1H), 8.48 (s, 2H), 8.37 (dd, 1H), 7.67 (d, 1H), 7.60 (d, 1H), 7.11 (d, 1H), 6.80 (m, 2H), 6.71-6.77 (m, 2H), 6.42 (s, 1H), 4.14 (s, 3H), 3.63 (q, 1H), 2.36 (dd, 1H), 2.30 (dd, 1H), 1.69-1.87 (m, 1H), 1.25 (d, 3H), 0.88 (d, 6H) |

Example 9

Preparation of Benzoic Acid 2-(3,5-dichloro-pyridin-4-yl)-1-(4-methoxy-8-amino-dibenzofuran-1-yl)-vinyl Ester (Compound 4)

Benzoic acid 2-(3,5-dichloro-pyridin-4-yl)-1-(4-methoxy-8-nitro-dibenzofuran-1-yl)-vinyl ester (675 mg, 1.26 mmoles) is dissolved in tetrahydrofuran (30 mL). Tin dichloride (SnCl₂*2H₂O, 2.84 g, 12.6 mmoles) is added and the resulting mixture is stirred at room temperature for 24 hours and at 40° C. for 3 hours. The mixture is diluted with water and a saturated NaHCO₃ solution and extracted with DCM; the combined organic layers are dried over sodium sulphate and evaporated to dryness. The crude (468 mg) is purified by preparative HPLC to yield 80 mg of pure product.

| Cpd | R₁ | R₂ | R₂' | Z | A | R₃ | X and Y | analytical |
|-----|----|----|----|---|---|----|---------|------------|
| 4 | Me | NH₂ | H | — | Ph | 3,5-Cl | Carbon atoms linked by a single bond | MS/ESI⁺ 505.07, 507.07 [MH]⁺; ¹H NMR (300 MHz, CDCl₃) δ ppm 8.56 (s, 2H), 7.92-8.00 (m, 2H), 7.82 (d, 1H), 7.54-7.61 (m, 1H), 7.52 (d, 1H), 7.43 (d, 1H), 7.37-7.45 (m, 2H), 7.00 (d, 1H), 6.84 (dd, 1H), 6.55 (s, 1H), 4.09 (s, 3H) |

Example 10

Preparation of Benzoic Acid 2-(3,5-dichloro-pyridin-4-yl)-1-(4-methoxy-8-methanesulphonylamino-dibenzofuran-1-yl)-vinyl Ester (Compound 5)

Crude benzoic acid 2-(3,5-dichloro-pyridin-4-yl)-1-(4-methoxy-8-amino-dibenzofuran-1-yl)-vinyl ester (1.17 g, obtained as described in Example 8 starting from 1.68 g of benzoic acid 2-(3,5-dichloro-pyridin-4-yl)-1-(4-methoxy-8-nitro-dibenzofuran-1-yl)-vinyl ester) is dissolved in dry DCM (5 mL) under nitrogen atmosphere. The solution is cooled to 0° C. and triethylamine (0.390 mL, 2.80 mmoles) and methanesulphonyl chloride (0.220 mL, 2.83 mmoles) are added sequentially dropwise. The resulting solution is stirred at room temperature for 1 hour. The mixture is diluted with water (2.5 mL) and saturated $NaHCO_3$ solution (10 mL) and extracted with DCM; the combined organic layers are dried over $Na_2SO_4$ and evaporated to dryness. The crude is purified by preparative HPLC to yield 330 mg of pure product as a white solid.

Example 11

Preparation of Benzoic Acid 1-(4-methoxy-8-nitro-dibenzofuran-1-yl)-2-(1-oxy-3,5-dichloro-pyridin-4-yl)-vinyl Ester (Compound 6)

Benzoic acid 2-(3,5-dichloro-pyridin-4-yl)-1-(4-methoxy-dibenzofuran-1-yl)-vinyl ester (89.2 mg, 0.182 mmoles) is dissolved in DCM (5 mL) under nitrogen atmosphere. m-Chloroperbenzoic acid (mCPBA, 81.8 mg, 0.365 mmoles) is added and the resulting mixture is stirred at room temperature for 5 hours, then an additional 81.8 mg of mCPBA are added and stirring is continued overnight (approximately 18 hours) to complete the conversion of the starting material. Excess solid sodium thiosulphite is added to the reaction mixture and the reaction is stirred at room temperature for 30 minutes; the solid by products are removed by filtration and the organic layer is washed sequentially with saturated aqueous $NaHCO_3$, water and brine. The crude product is purified by flash chromatography on $SiO_2$ (DCM/AcOEt=from 95:5 to 50:50) to yield the desired product as off-white solid (40 mg).

| Cpd | $R_1$ | $R_2$ | $R_2'$ | Z | A | $R_3$ | X and Y | analytical |
|---|---|---|---|---|---|---|---|---|
| 5 | Me | $NHSO_2CH_3$ | H | — | Ph | 3,5-Cl | Carbon atoms linked by a single bond | MS/ESI+ 583.04, 585.04 [MH]+; $^1$H NMR (300 MHz, $CDCl_3$) δ ppm Z isomer: 8.58 (s, 2H), 8.39 (d, 1H), 7.93-8.02 (m, 2H), 7.66 (d, 1H), 7.52-7.61 (m, 1H), 7.43 (m, 2H), 7.40-7.48 (m, 2H), 7.10 (d, 1H), 6.56 (s, 1H), 6.24 (s, 1H), 4.13 (s, 3H), 2.88 (s, 3H) E isomer: 8.40 (s, 2H), 8.31 (d, 1H), 8.10-8.18 (m, 2H), 7.51-7.73 (m, 1H), 7.32-7.51 (m, 4H), 7.14 (d, 1H), 6.82 (d, 1H), 6.75 (s, 1H), 6.40 (s, 1H), 4.02 (s, 3H), 2.96 (s, 3H) |

The following compounds are prepared following the same route using suitable reagents:

| Cpd | R₁ | R₂ | R₂' | Z | A | R₃ | X and Y | analytical |
|---|---|---|---|---|---|---|---|---|
| 6 | Me | NO₂ | H | — | Ph | 3,5-Cl | Carbon atoms linked by a single bond | MS/ESI⁺ 551.33, 553.33 [MH]⁺; ¹H NMR (300 MHz, CDCl₃) δ ppm Z isomer: 9.39 (d, 1H), 8.72 (s, 2H), 8.44 (dd, 1H), 8.02 (d, 1H), 7.96 (dd, 2H), 7.71 (d, 1H), 7.65 (t, 1H), 7.46-7.55 (m, 2H), 7.43 (d, 1H), 6.81 (s, 1H), 4.08 (s, 3H) |
| 6 | Me | NO₂ | H | — | Ph | 3,5-Cl | Carbon atoms linked by a single bond | MS/ESI⁺ 551.33, 553.33 [MH]⁺; ¹H NMR (300 MHz, CDCl₃) δ ppm E isomer: 9.21 (d, 1H), 8.53 (s, 2H), 8.46 (dd, 1H), 8.03-8.10 (m, 2H), 8.01 (d, 1H), 7.81-7.90 (m, 2H), 7.57-7.63 (m, 1H), 7.24 (d, 1H), 7.18 (d, 1H), 6.93 (s, 1H), 4.00 (s, 3H) |
| 7 | Me | H | H | — | Ph | 3,5-Cl | Carbon atoms linked by a single bond | MS/ESI⁺ 506.10, 508.10 [MH]⁺; ¹H NMR (300 MHz, CDCl₃) δ ppm E isomer: 8.39 (ddd, 0H), 8.07 (s, 2H), 8.03-8.12 (m, 2H), 7.60-7.69 (m, 2H), 7.56 (d, 1H), 7.51-7.60 (m, 1H), 7.36-7.51 (m, 3H), 7.11 (d, 1H), 6.84 (d, 1H), 6.63 (s, 1H), 4.06 (s, 3H) Z isomer: 8.45 (dd, 1H), 8.06 (s, 1H), 7.92-8.01 (m, 2H), 7.35-7.68 (m, 8H), 7.05 (d, 1H), 6.49 (s, 1H), 4.12 (s, 3H) |
| 8 | Me | NHSO₂Me | H | — | Ph | 3,5-Cl | Carbon atoms linked by a single bond | MS/ESI⁺ 599.32, 601.32 [MH]⁺; ¹H NMR (300 MHz, CDCl₃) δ ppm Z isomer: 9.75 (s, 1H), 8.68 (s, 2H), 8.28 (d, 1H), 7.97-8.03 (m, 2H), 7.74 (d, 1H), 7.62-7.71 (m, 1H), 7.57 (d, 1H), 7.49 (t, 2H), 7.40 (dd, 1H), 7.30 (d, 1H), 6.66 (s, 1H), 4.04 (s, 3H), 2.84 (s, 3H) E isomer: 9.88 (s, 1H), 8.52 (s, 2H), 8.31 (d, 1H), 8.07-8.17 (m, 2H), 7.83-7.95 (m, 1H), 7.63-7.71 (m, 1H), 7.47-7.53 (m, 2H), 7.41-7.47 (m, 1H), 7.10 (d, 1H), 7.06 (d, 1H), 6.82 (s, 1H), 3.95 (s, 3H), 2.95 (s, 3H) |

Example 12

Preparation of 1-(4-methoxy-8-nitro-dibenzofuran-1-yl)-2-(3,5-dichloro-pyridin-4-yl)-ethanol (6a) (According to Scheme 1)

Sodium boron hydride $NaBH_4$ (92 mg, 2.43 mmoles) is added to a suspension of compound 5a (700 mg, 1.62 mmoles) in EtOH (50 mL), DCM (100 mL) and tetrahydrofuran (100 mL) at room temperature. The mixture is stirred at room temperature for 3 days to obtain complete conversion. The reaction mixture is evaporated to dryness, the residue is suspended in MeOH (60 mL) and the desired product is recovered as a light-yellow solid by filtration (470 mg). The compound is employed in the next step without further purification.

The following compounds are prepared following the same synthetic procedure, using suitable reagents:

|    | $R_1$ | $R_2$ | $R_2{}'$ | $R_3$ | X and Y | analytical |
|----|-------|-------|----------|-------|---------|------------|
| 6a | Me | $NO_2$ | H | 3,5-Cl | Carbon atoms linked by a single bond | MS/ESI⁺ 433.2, 435.2 [MH]⁺ |
| 6b | Me | H | H | 3,5-Cl | Carbon atoms linked by a single bond | MS/ESI⁺ 388.1, 390.1 [MH]⁺ |

Example 13

Preparation of 2-(3,5-dichloro-pyridin-4-yl)-1-[4-methoxy-3-(4-nitro-phenoxy)-phenyl]-ethanol (6c) (According to Scheme 1)

3,5-dichloro-4-methyl-pyridine (0.65 g, 4.0 mmoles) is dissolved in dry tetrahydrofuran (12 mL) under nitrogen atmosphere and the resulting solution is cooled to −60° C. Lithium bis(trimethylsilyl) amide (1N solution in tetrahydrofuran, 4.4 mL, 4.4 mmoles) is added dropwise and the mixture is stirred at −60° C. for 1 hour. Compound (1b) (1.1 g, 4.0 mmoles) dissolved in dry tetrahydrofuran (12 mL) is then added and the reaction mixture is stirred at room temperature for 2 hours. The reaction is quenched by addition of a saturated $NH_4Cl$ aqueous solution and extracted with AcOEt. The organic layer is dried over $Na_2SO_4$ and the solvent is evaporated. The crude mixture is purified by chromatography on $SiO_2$ (eluent:hexane:AcOEt=from 8:2 to 7:3) to yield 1.6 g of the pure title compound.

| $R_1$ | $R_2$ | $R_2{}'$ | $R_3$ | analytical |
|-------|-------|----------|-------|------------|
| Me | $NO_2$ | H | 3,5-Cl | MS/ESI⁺ 435.2, 437.2 [MH]⁺ |

Example 14

Preparation of 3-cyclopropylmethoxy-4-difluoromethoxybenzoic Acid

Step 1. Preparation of 4-difluoromethoxy-3-hydroxybenzaldehyde

Sodium hydroxide (4.8 g, 120 mmoles) is added to a solution of 3,4-dihydroxybenzaldehyde (16.6 g, 120 mmol) and sodium chlorodifluoroacetate (18.3 g, 120 mmol) in dimethylformamide (150 mL) and water (3 mL). The mixture is heated to 120° C. and stirred at this temperature for 2 hours. The solvent is removed by vacuum distillation and aqueous hydrochloric acid (20 mL) is added to the residue. The mixture is extracted with diethyl ether (2×50 ml), the combined organic layers are washed with water and brine and the solvent removed under reduced pressure. The crude product is purified by chromatography on silica gel (hexane/ethyl acetate 8:2) to furnish 4-difluoromethoxy-3-hydroxybenzaldehyde as a colourless solid (10 g).

Step 2. Preparation of 3-cyclopropylmethoxy-4-difluoromethoxybenzaldehyde

A mixture of 4-difluoromethoxy-3-hydroxybenzaldehyde (10 g, 53 mmol) and potassium carbonate (44 g, 105 mmol) in tetrahydrofuran (100 mL) is cooled to 0° C. and a solution of bromomethylcyclopropane (11 mL, 116.6 mmol) in tetrahydrofuran (50 mL) is added under vigorous stirring. The reaction mixture is heated to reflux under stirring for 7 hours, then fresh bromomethylcyclopropane (5.5 mL, 58.3 mmoles) is added and heating is continued for further 7 hours. The reaction mixture is cooled to room temperature and 2 N sodium hydroxide (100 ml) is added; the aqueous layer is extracted with dichloromethane (2×100 mL), the combined organic layers are dried over $Na_2SO_4$ and the solvent is removed under reduced pressure to afford 3-cyclopropylmethoxy-4-difluoromethoxybenzaldehyde (12 g), that is used in the next step without further purification.

Step 3. Preparation of 3-cyclopropylmethoxy-4-difluoromethoxybenzoic Acid 3-cyclopropylmethoxy-4-difluoromethoxybenzaldehyde (12 g, 50 mmol) and sulfamic acid (7.3 g, 75 mmol) are dissolved in glacial acetic acid (50 mL) and a solution of sodium chloride (8.2 g, 75 mmol) in water (15 mL) is added. The reaction mixture is stirred at room temperature for 1 hour, then water (300 ml) is added to obtain the precipitation of the desired product that is filtered and dried at 40° C. under vacuum (12 g).

Example 15

Preparation of Benzoic Acid 1-(4-methoxy-8-nitro-dibenzofuran-1-yl)-2-(3,5-dichloro-pyridin-4-yl)-ethyl Ester (Compound 9)

Compound (6a) (140 mg, 0.32 mmoles) is dissolved in pyridine (5 mL) and benzoyl chloride (0.37 mL, 3.2 mmoles) is added. The mixture is heated in a sealed vial in a microwave reactor at +90° C. for 60 minutes. The reaction mixture is then evaporated to dryness, the residue is dissolved in DCM (20 mL) and extracted with 1N NaOH (10 mL) and 1N HCl (2×20 mL). The organic layer is dried over $Na_2SO_4$ and evaporated to dryness. The crude is purified by flash chromatography on $SiO_2$ (AcOEt:hexane=from 0:100 to 3:7) to yield 80 mg of the title compound The following compounds are prepared following the same synthetic procedure, using suitable reagents:

| Cpd | $R_1$ | $R_2$ | $R_2'$ | Z | A | $R_3$ | X and Y | analytical |
|---|---|---|---|---|---|---|---|---|
| 9 | Me | $NO_2$ | H | — | Ph | 3,5-Cl | Carbon atoms linked by a single bond | MS/ESI$^+$ 538.36, 540.36 [MH]$^+$ |
| 10 | Me | H | H | — | Ph | 3,5-Cl | Carbon atoms linked by a single bond | MS/ESI$^+$ 493.36, 495.36 [MH]$^+$ |

Example 16

Preparation of 3-Cyclopropylmethoxy-4-difluoromethoxy Benzoic Acid 2-(3,5-dichloro-pyridin-4-yl)-1-[4-methoxy-3-(4-nitro-phenoxy)-phenyl]-ethyl Ester (Compound 11).

3-cyclopropylmethoxy-4-difluoromethoxybenzoic acid (268 mg, 1.04 mmoles) is dissolved in dry tetrahydrofuran (30 mL) and EDC (237 mg, 1.24 mmoles), HOBT (190 mg, 1.24 mmoles), TEA (0.172 mL, 1.24 mmoles), DMAP (30 mg) are added to the solution. The mixture is stirred at room temperature for 40 minutes, then Benzoic acid 1-(4-methoxy-8-nitro-dibenzofuran-1-yl)-2-(3,5-dichloro-pyridin-4-yl)-ethyl ester is added and the reaction mixture is stirred at 70° C. for 32 hours. The solvents are then evaporated and the crude mixture is purified by chromatography on $SiO_2$ (hexane:AcOEt from 10:1 to 7:3) to afford 300 mg of the pure title compound.

| Cpd | $R_1$ | $R_2$ | $R_2'$ | Z | A | $R_3$ | X and Y | analytical |
|---|---|---|---|---|---|---|---|---|
| 11 | Me | $NO_2$ | H | — | 3-CyPrCH$_2$O 4-diFCHO-Ph | 3,5-Cl | Carbon atoms substituted with a hydrogen atom | MS/ESI$^+$ 675.22, 677.22 [MH]$^+$ |

Example 17

Preparation of Benzoic Acid 1-(4-methoxy-8-nitro-dibenzofuran-1-yl)-2-(1-oxy-3,5-dichloro-pyridin-4-yl)-ethyl Ester (Compound 12)

Benzoic acid 1-(4-methoxy-dibenzofuran-1-yl)-2-(3,5-dichloro-pyridin-4-yl)-ethyl ester (300 mg, 0.45 mmoles) is dissolved in DCM (30 mL) under nitrogen atmosphere. m-Chloroperbenzoic acid (mCPBA, 774 mg, 3.15 mmoles) is added and the resulting mixture is stirred at room temperature for 24 hours to complete the conversion of the starting material. Excess solid sodium thiosulphite is added to the reaction mixture and the reaction is stirred at room temperature for 30 minutes; the solid by products are removed by filtration and the organic layer is washed sequentially with saturated aqueous $NaHCO_3$, water and brine. The organic layer is dried over $Na_2SO_4$ and evaporated to dryness. The crude mixture is purified by chromatography on $SiO_2$ (hexane:AcOEt from 20:1 to 1:1) and subsequently by preparative HPLC to afford 100 mg of the pure title compound.

The following compounds are prepared following the same synthetic procedure, using suitable reagents:

| Cpd | $R_1$ | $R_2$ | $R_2'$ | Z | A | $R_3$ | X and Y | analytical |
|---|---|---|---|---|---|---|---|---|
| 12 | Me | $NO_2$ | H | — | Ph | 3,5-Cl | Carbon atoms linked by a single bond | MS/ESI$^+$ 554.36, 556.36 [MH]$^+$ |
| 13 | Me | H | H | — | Ph | 3,5-Cl | Carbon atoms linked by a single bond | MS/ESI$^+$ 509.36, 511.36 [MH]$^+$ |
| 14 | Me | $NO_2$ | H | — | 3-CyPrCH$_2$O 4-diFCHO-Ph | 3,5-Cl | Carbon atoms linked by a single bond | MS/ESI$^+$ 691.27, 693.27 [MH]$^+$; $^1$H NMR (300 MHz, CDCl$_3$) δ ppm 8.55 (s, 2H), |

| Cpd | R$_1$ | R$_2$ | R$_2$' | Z A | R$_3$ | X and Y | analytical |
|---|---|---|---|---|---|---|---|
| | | | | | | | 8.22 (m, 2H), 7.63 (dd, 1H), 7.60 (d, 1H), 7.44 (dd, 1H), 7.36 (d, 1H), 7.29 (d, 1H), 7.26 (d, 1H), 7.22 (t, 1H), 6.97 (m, 2H), 6.22 (dd, 1H), 3.86-4.01 (m, 2H), 3.74 (s, 3H), 3.62 (dd, 1H), 3.34-3.44 (m, 1H), 1.15-1.32 (m, 1H), 0.48-0.65 (m, 2H), 0.26-0.43 (m, 2H) |
| 17 | Me | H | H | 2-Piperidin-1-yl-ethoxy | 3,5-Cl | Carbon atoms linked by a single bond | MS/ESI$^+$ 636.55, 638.55 [MH]$^+$ |
| 18 | Me | NO$_2$ | H | 3-CyPrCH2O 4-diFCHO-Ph | 3,5 | Carbon atoms linked by a single bond | MS/ESI$^+$ 690.46, 692.46 [MH]$^+$ |

Pharmacological Activity.

Example 18

In Vitro Determination of PDE4 Inhibitory Activity in the Cell Free Assay

The U937 human monocytic cell line is used as source of PDE4 enzyme. Cells are cultured, harvested and supernatant fraction prepared essentially as described in Torphy T J et al., *J. Pharmacol. Exp. Ther.*, 1992; 263:1195-1205. PDE4 activity is determined in cells supernatants by assaying cAMP disappearance from the incubation mixtures. 50 µl of cell supernatant are incubated at 30° C. for 30 minutes in a final volume of 200 µl in the presence of 1.6 µM cAMP with or without the test compound (50 µl). The concentration of the test compounds ranges between $10^{-12}$ M and $10^{-6}$ M. Reactions are stopped by heat inactivation (2.5 minutes at 100° C.) and residual cAMP is measured using an electrochemiluminescence (ECL)-based immunoassay. The results are expressed as mean±95% confidence limits of the molar concentration of the test compound producing 50% inhibition of cAMP disappearance (IC$_{50}$). The compounds 1, 2, 4, 5, and 7 are tested and their values of IC$_{50}$ in the cell free assay turn out to be comprised between 1 and 70 nM. Percentage of inhibition of PDE4 activity is calculated, assuming cAMP disappearance in the absence of inhibitors as 100% and cAMP disappearance in heat inactivated samples as 0%.

Example 19

In Vitro Determination of PDE4 Inhibitory Activity in the Peripheral Blood Mononuclear Cells (PBMCs) Assay The assay, which is based on the known inhibitory activity exerted by PDE4 inhibitors on the lipopolyshaccarides (LPS)-induced tumour necrosis factor-alpha (TNF-α release in peripheral blood mononuclear cells (PBMCs), is performed according to a method previously described (Hatzelmann A et al., *J. Pharmacol. Exp. Ther.*, 2001; 297:267-279; and Draheim R et al., *J. Pharmacol. Exp. Ther.*, 2004; 308: 555-563. Cryopreserved human PBMCs, (100 µl/well) are incubated in 96-well plates ($10^5$ cells/well), for 30 minutes, in the presence or absence (50 microl) of the test compounds whose concentrations ranged from $10^{-12}$ M to $10^{-6}$ M. Subsequently, LPS (3 ng/ml) is added. After 18 hours of incubation at 37° C. in a humidified incubator under an atmosphere of 95% air and 5% CO$_2$, culture medium is collected and TNF-α measured by ELISA.

The results are expressed as mean±95% confidence limits of the molar concentration of the test compound producing 50% inhibition of LPS-induced TNF-α release (IC$_{50}$). The compounds 1, 2, 4, 5, and 7 are tested and their values of IC$_{50}$ in the PBMCs assay turned out to be comprised between 1 and 150 nM. The effects of the tested compounds are calculated as percentage of inhibition of TNF-α release, assuming LPS-induced TNF-α production in the absence of inhibitor compound as 100% and basal TNF-α production of PBMCs in the absence of LPS as 0%.

Example 20

Evaluation of the Ability to Inhibit the Low Affinity LPDE4 Versus the Ability to Compete for the High Affinity HPDE4

The affinity toward LPDE4 and HPDE4 is assessed as previously described respectively in Cortijo J et al., *Br. J. Pharmacol.*, 1993, 108: 562-568 and Duplantier A J et al., *J. Med. Chem.*, 1996; 39: 120-125. The activity of compounds 1, 2, 4, 5, 6, and 7 is evaluated. The concentration of the test compounds ranges between $10^{-12}$ M and $10^{-5}$ M. In the case of LPDE4, the IC$_{50}$ is the molar concentration of the test compound producing 50% inhibition of cAMP disappearance, while in the case of HPDE4, the IC$_{50}$ is the molar concentration of the test compound producing 50% inhibition of the binding of [H$^3$]rolipram. The results indicate that the representative compounds of the invention inhibit LPDE4 with nanomolar affinity. Said compounds turned out to be from 70 to 811-fold more selective toward LPDE4 versus HPDE4.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I)

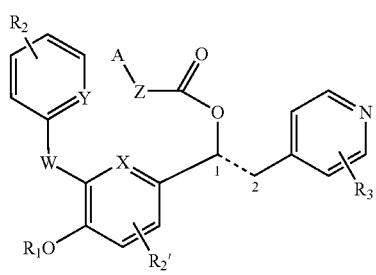

wherein:
the broken line between atoms 1 and 2 represents a single or a double bond;
X and Y may be carbon atoms substituted with a hydrogen atom or $R_2'$ and $R_2$, respectively, or carbon atoms linked by a single bond;
W is;
Z is
$(CH_2)_n$ wherein n=0, 1 or 2;
$R_1$ is selected from the group consisting of
H;
$C_1$-$C_6$ alkyl, optionally substituted by one or more substituents selected from the group consisting of $C_3$-$C_7$ cycloalkyl and $C_3$-$C_7$ cycloalkenyl;
$C_3$-$C_7$ cycloalkyl;
$C_3$-$C_7$ cycloalkenyl;
$C_2$-$C_6$ alkenyl and
$C_2$-$C_6$ alkynyl;
when X and Y are not linked by a single bond, there may be one, two, three, four, or five $R_2$ substituents and there may be one, two, or three $R_2'$ substituents, and when X and Y are linked by a single bond, there may be one, two, three, or four $R_2$ substituents and there may be one or two $R_2'$ substituents, and each $R_2$ and $R_2'$ is independently one or more groups selected from the group consisting of
H;
$C_1$-$C_6$ alkyl, optionally substituted by one or more substituents selected from the group consisting of $C_3$-$C_7$ cycloalkyl and $C_3$-$C_7$ cycloalkenyl;
$C_3$-$C_7$ cycloalkyl;
$C_3$-$C_7$ cycloalkenyl;
$C_2$-$C_6$ alkenyl;
$C_2$-$C_6$ alkynyl;
halogen atoms;
cyano;
nitro;
$NR_8R_9$ wherein $R_8$ and $R_9$ are different or the same and are independently selected from the group consisting of
H;
$C_1$-$C_6$ alkyl, optionally substituted with phenyl;
$COC_6H_5$;
$COC_1$-$C_4$ alkyl;
or together with the nitrogen atom to which they are linked form a saturated or partially saturated ring, preferably a piperidyl ring;
$OR_{10}$ or $COR_{10}$ wherein $R_{10}$ is phenyl, $C_1$-$C_6$ alkyl, $C_1$-$C_6$ alkynyl, or $C_1$-$C_6$ alkenyl;
oxo;
$HNSO_2R_{11}$ wherein $R_{11}$ is $C_1$-$C_6$ alkyl or a phenyl optionally substituted with halogen atoms or with a $C_1$-$C_6$ alkyl group;
$SO_2R_{12}$ wherein $R_{12}$ is $C_1$-$C_6$ alkyl, OH, or $NR_8R_9$ wherein $R_8$ and $R_9$ are as defined above;
$SOR_{13}$ wherein $R_{13}$ is phenyl, or $C_1$-$C_6$ alkyl;
$SR_{14}$ wherein $R_{14}$ is H, phenyl, or $C_1$-$C_6$ alkyl;
$COOR_{15}$ wherein $R_{15}$ is H, $C_1$-$C_6$ alkyl, phenyl, benzyl; and
$(CH_2)_rOR_{16}$, wherein r=1, 2, 3 or 4 and $R_{16}$ is H or $C_1$-$C_6$ cycloalkyl;
there may be one, two, three, or four $R_3$ substituents and each $R_3$ is independently selected from the group consisting of H, cyano, nitro, $CF_3$ and halogen atoms, preferably chlorine;
A is an optionally substituted ring system in which the optional substituent $R_x$ consists of one or more groups, which may be the same or different, and are independently selected from the group consisting of:
$C_1$-$C_6$ alkyl optionally substituted by one or more $C_3$-$C_7$ cycloalkyl;
$C_2$-$C_6$ alkenyl optionally substituted by one or more $C_3$-$C_7$ cycloalkyl;
$C_2$-$C_6$ alkynyl optionally substituted by one or more $C_3$-$C_7$ cycloalkyl;
$C_3$-$C_7$ cycloalkyl;
$C_3$-$C_7$ cycloalkenyl;
$OR_{17}$ wherein $R_{17}$ is selected from the group consisting of
H;
$C_1$-$C_6$ alkyl optionally substituted by one or more $C_3$-$C_7$ cycloalkyl;
$C_3$-$C_7$ cycloalkyl;
phenyl;
benzyl;
$C_1$-$C_6$ alkyl-$NR_{18}R_{19}$ wherein $R_{18}$ and $R_{19}$ are independently selected from the group consisting of H and $C_1$-$C_6$ alkyl or they form with the nitrogen atom to which they are linked a saturated or partially saturated ring, preferably a piperidyl ring;
halogen atoms;
cyano;
nitro;
$NR_8R_9$ wherein $R_8$ and $R_9$ are as defined above;
$OR_{10}$ or $COR_{10}$ wherein $R_{10}$ is as defined above
oxo;
$HNSO_2R_{11}$ wherein $R_{11}$ is $C_1$-$C_6$ alkyl or a phenyl optionally substituted with halogen atoms or with a $C_1$-$C_6$ alkyl group;
$SO_2R_{12}$ wherein $R_{12}$ is $C_1$-$C_6$ alkyl, OH, or $NR_8R_9$ wherein $R_8$ and $R_9$ are as defined above;
$SOR_{13}$ wherein $R_{13}$ is phenyl or $C_1$-$C_6$ alkyl;
$SR_{14}$ wherein $R_{14}$ is H, phenyl, or $C_1$-$C_6$ alkyl;
$COOR_{15}$ wherein $R_{15}$ is H, $C_1$-$C_6$ alkyl, phenyl, benzyl; and
$(CH_2)_rOR_{16}$, wherein r=1, 2, 3 or 4 and $R_{16}$ is H or $C_1$-$C_6$ cycloalkyl
or a pharmaceutically acceptable salt thereof or a pyridine ring N-oxide thereof.

2. A compound of claim 1, pharmaceutically acceptable salt thereof, or pyridine ring N-oxide thereof, wherein A is an optionally substituted phenyl.

3. A compound of claim 1, pharmaceutically acceptable salt thereof, or pyridine ring N-oxide thereof, wherein A is a heteroaryl ring selected from the group consisting of pyrrole, pyrazole, furan, thiophene, imidazole, oxazole, isoxazole, thiazole, pyridine, pyrimidine, pyrazine, pyridazine and pyran.

4. A compound of claim 1, pharmaceutically acceptable salt thereof, or pyridine ring N-oxide thereof, wherein $R_3$ is a halogen atom.

5. A compound of claim 4, pharmaceutically acceptable salt thereof, or pyridine ring N-oxide thereof, wherein $R_3$ is chlorine.

6. A compound of claim 5, represented by formula (II)

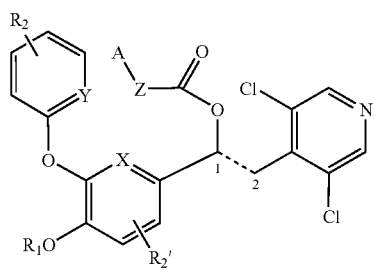

(II)

or a pharmaceutically acceptable salt thereof, or a pyridine ring N-oxide thereof.

7. A compound of claim 6, represented by formula (IIA)

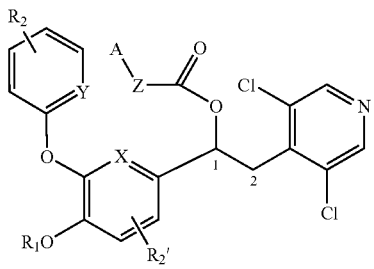

(IIA)

or a pharmaceutically acceptable salt thereof, or a pyridine ring N-oxide thereof.

8. A compound of claim 7, represented by formula (IIA')

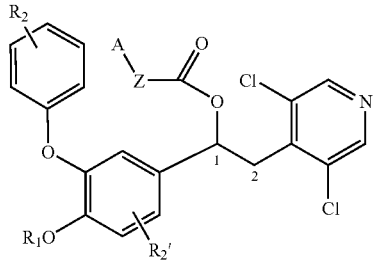

(IIA')

or a pharmaceutically acceptable salt thereof, or a pyridine ring N-oxide thereof.

9. A compound of claim 8, pharmaceutically acceptable salt thereof, or pyridine ring N-oxide thereof, wherein Z is $(CH_2)_n$ wherein n is 0 and A is optionally substituted phenyl.

10. A compound of claim 7 represented by formula (IIA")

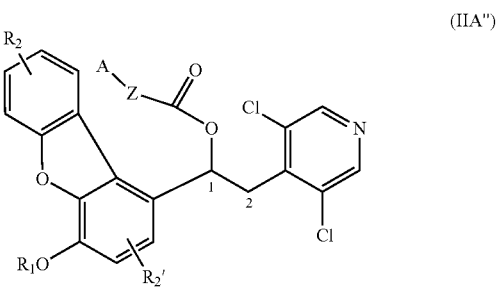

(IIA")

or a pharmaceutically acceptable salt thereof, or a pyridine ring N-oxide thereof.

11. A compound of claim 10, pharmaceutically acceptable salt thereof, or pyridine ring N-oxide thereof, wherein Z is $(CH_2)_n$ wherein n is 0 and A is optionally substituted phenyl.

12. A compound of claim 6, represented by formula (IIB)

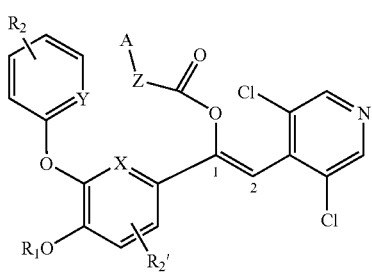

(IIB)

or a pharmaceutically acceptable salt thereof, or a pyridine ring N-oxide thereof.

13. A compound of claim 12, represented by formula (IIB')

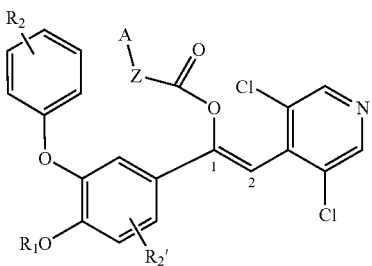

(IIB')

or a pharmaceutically acceptable salt thereof, or a pyridine ring N-oxide thereof.

14. A compound of claim 13, pharmaceutically acceptable salt thereof, or pyridine ring N-oxide thereof, wherein Z is $(CH_2)_n$ wherein n is 0 and A is optionally substituted phenyl.

15. A compound of claim 12, represented by formula (IIB")

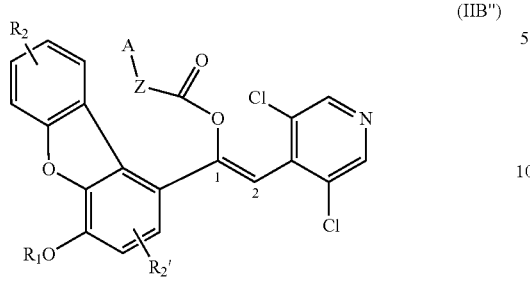

(IIB")

or a pharmaceutically acceptable salt thereof, or a pyridine ring N-oxide thereof.

16. A compound of claim 15, pharmaceutically acceptable salt thereof, or pyridine ring N-oxide thereof, wherein Z is $(CH_2)_n$ wherein n is 0 and A is optionally substituted phenyl.

17. A compound, which is selected from the following:

Benzoic acid 2-(3,5-dichloro-pyridin-4-yl)-1-(4-methoxy-8-nitro-dibenzofuran-1-yl)-vinyl ester, Benzoic acid 2-(3,5-dichloro-pyridin-4-yl)-1-(4-methoxy-dibenzofuran-1-yl)-vinyl ester, (S)-2-(4-Isobutyl-phenyl)-propionic acid 2-(3,5-dichloro-pyridin-4-yl)-1-(4-methoxy-8-nitro-dibenzofuran-1-yl)-vinyl ester, Benzoic acid 2-(3,5-dichloro-pyridin-4-yl)-1-(4-methoxy-8-amino-dibenzofuran-1-yl)-vinyl ester, Benzoic acid 2-(3,5-dichloro-pyridin-4-yl)-1-(8-methanesulfonylamino-4-methoxy-dibenzofuran-1-yl)-vinyl ester, Benzoic acid 2-(3,5-dichloro-1-oxy-pyridin-4-yl)-1-(4-methoxy-8-nitro-dibenzofuran-1-yl)-vinyl ester, Benzoic acid 2-(3,5-dichloro-1-oxy-pyridin-4-yl)-1-(4-methoxy-dibenzofuran-1-yl)-vinyl ester, Benzoic acid 1-(4-methoxy-8-methanesulphonylamino-dibenzofuran-1-yl)-2-(1-oxy-3,5-dichloro-pyridin-4-yl)-vinyl ester, Benzoic acid 2-(3,5-dichloro-pyridin-4-yl)-1-(4-methoxy-8-nitro-dibenzofuran-1-yl)-ethyl ester, Benzoic acid 2-(3,5-dichloro-pyridin-4-yl)-1-(4-methoxy-dibenzofuran-1-yl)ethyl ester, 3-Cyclopropylmethoxy-4-difluoromethoxy benzoic acid 2-(3,5-dichloro-pyridin-4-yl)-1-[4-methoxy-3-(4-nitrophenoxy)-phenyl]-ethyl ester, Benzoic acid 1-(4-methoxy-8-nitro-dibenzofuran-1-yl)-2-(1-oxy-3,5-dichloro-pyridin-4-yl)-ethyl ester, Benzoic acid 1-(4-methoxy-dibenzofuran-1-yl)-2-(1-oxy-3,5-dichloro-pyridin-4-yl)-ethyl ester, 3-Cyclopropylmethoxy-4-difluoromethoxy-benzoic acid 2-(3,5-dichloro-1-oxy-pyridin-4-yl)-1-[4-methoxy-3-(4-nitro-phenoxy)-phenyl]-ethyl ester, Benzoic acid 1-(3-chloro-4-methoxy-dibenzofuran-1-yl)-2-(3,5-dichloro-1-oxy-pyridin-4-yl)-ethyl ester, 2-(4-Isobutyl-phenyl)-propionic acid 2-(3,5-dichloro-pyridin-4-yl)-1-(4-methoxy-8-nitro-dibenzofuran-1-yl)-ethyl ester), 4-Methoxy-8-nitro-dibenzofuran-1-carboxylic acid 2-(3,5-dichloro-pyridin-4-yl)-1-(4-methoxy-8-nitro-dibenzofuran-1-yl)-vinyl ester, pharmaceutically acceptable salts thereof, and pyridine ring N-oxides thereof.

18. A compound of claim 17, which is (S)-2-(4-Isobutyl-phenyl)-propionic acid 2-(3,5-dichloro-pyridin-4-yl)-1-(4-methoxy-8-nitro-dibenzofuran-1-yl)-vinyl ester, a pharmaceutically acceptable salt thereof, or a pyridine ring N-oxide thereof.

19. A compound of claim 17, which is Benzoic acid 2-(3,5-dichloro-pyridin-4-yl)-1-(4-methoxy-8-amino-dibenzofuran-1-yl)-vinyl ester, a pharmaceutically acceptable salt thereof, or a pyridine ring N-oxide thereof.

20. A compound of claim 17, which is Benzoic acid 1-(4-methoxy-8-methanesulphonylamino-dibenzofuran-1-yl)-2-(1-oxy-3,5-dichloro-pyridin-4-yl)-vinyl ester, a pharmaceutically acceptable salt thereof, or a pyridine ring N-oxide thereof.

21. A compound of claim 17, which is Benzoic acid 2-(3,5-dichloro-pyridin-4-yl)-1-(8-methanesulfonylamino-4-methoxy-dibenzofuran-1-yl)-vinyl ester, a pharmaceutically acceptable salt thereof, or a pyridine ring N-oxide thereof.

22. A compound of claim 17, which is Benzoic acid 2-(3,5-dichloro-1-oxy-pyridin-4-yl)-1-(4-methoxy-dibenzofuran-1-yl)-vinyl ester, a pharmaceutically acceptable salt thereof, or a pyridine ring N-oxide thereof.

23. A compound of claim 17, which is Benzoic acid 2-(3,5-dichloro-1-oxy-pyridin-4-yl)-1-(4-methoxy-8-nitro-dibenzofuran-1-yl)-vinyl ester, a pharmaceutically acceptable salt thereof, or a pyridine ring N-oxide thereof.

24. A compound of claim 17, which is 4 Methoxy-8-nitro-dibenzofuran-1-carboxylic acid 2-(3,5-dichloro-pyridin-4-yl)-1-(4-methoxy-8-nitro-dibenzofuran-1-yl)-vinyl ester, a pharmaceutically acceptable salt thereof, or a pyridine ring N-oxide thereof.

25. A compound of claim 17, which is Benzoic acid 2-(3,5-dichloro-pyridin-4-yl)-1-(4-methoxy-8-nitro-dibenzofuran-1-yl)-vinyl ester, a pharmaceutically acceptable salt thereof, or a pyridine ring N-oxide thereof.

26. A compound of claim 17, which is Benzoic acid 2-(3,5-dichloro-pyridin-4-yl)-1-(4-methoxy-dibenzofuran-1-yl)-vinyl ester, a pharmaceutically acceptable salt thereof, or a pyridine ring N-oxide thereof.

27. A compound of formula (I)

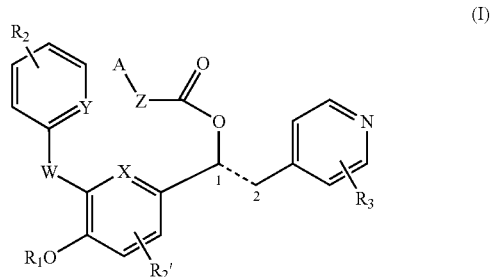

(I)

wherein:

the broken line between atoms 1 and 2 represents a single or a double bond;

X and Y may be carbon atoms substituted with a hydrogen atom or $R_2'$ and $R_2$, respectively, or carbon atoms linked by a single bond;

W is;

Z is $(CH_2)_n$ wherein n=0, 1 or 2;

$R_1$ is selected from the group consisting of

H and $C_1$-$C_6$ alkyl, optionally substituted by one or more substituents selected from the group consisting of $C_3$-$C_7$ cycloalkyl and $C_3$-$C_7$ cycloalkenyl;

when X and Y are not linked by a single bond, there may be one, two, three, four, or five $R_2$ substituents and there may be one, two, or three $R_2'$ substituents, and when X and Y are linked by a single bond, there may be one, two, three, or four $R_2$ substituents and there may be one or two $R_2'$ substituents, and each $R_2$ and $R_2'$ is independently one or more groups selected from the group consisting of

H;

nitro;

$NR_8R_9$ wherein $R_8$ and $R_9$ are different or the same and are independently selected from the group consisting of H and $C_1$-$C_6$ alkyl, optionally substituted with phenyl; and $HNSO_2R_{11}$ wherein $R_{11}$ is $C_1$-$C_6$ alkyl or a phenyl optionally substituted with halogen atoms or with a $C_1$-$C_6$ alkyl group;

there may be one, two, three, or four $R_3$ substituents and each $R_3$ is independently selected from the group consisting of halogen atoms;

A is an optionally substituted ring system in which the optional substituent $R_x$ consists of one or more groups, which may be the same or different, and are independently selected from the group consisting of:

$C_1$-$C_6$ alkyl optionally substituted by one or more $C_3$-$C_7$ cycloalkyl;

$OR_{17}$ wherein $R_{17}$ is selected from the group consisting of $C_1$-$C_6$ alkyl optionally substituted by one or more $C_3$-$C_7$ cycloalkyl;

$C_3$-$C_7$ cycloalkyl;

halogen atoms;

nitro;

or a pharmaceutically acceptable salt thereof or a pyridine ring N-oxide thereof.

28. A compound of claim 27, pharmaceutically acceptable salt thereof, or pyridine ring N-oxide thereof, wherein A is an optionally substituted phenyl.

29. A compound of claim 27, pharmaceutically acceptable salt thereof, or pyridine ring N-oxide thereof, wherein A is a heteroaryl ring selected from the group consisting of pyrrole, pyrazole, furan, thiophene, imidazole, oxazole, isoxazole, thiazole, pyridine, pyrimidine, pyrazine, pyridazine and pyran.

30. A compound of claim 27, pharmaceutically acceptable salt thereof, or pyridine ring N-oxide thereof, wherein $R_3$ is a halogen atom.

31. A compound of claim 30, pharmaceutically acceptable salt thereof, or pyridine ring N-oxide thereof, wherein $R_3$ is chlorine.

32. A pharmaceutical composition, comprising a compound according to claim 1, a pharmaceutically acceptable salt thereof, or a pyridine ring N-oxide thereof, and one or more pharmaceutically acceptable carriers and/or excipients.

33. A pharmaceutical composition according to claim 32, which is in a form suitable for administration by inhalation.

34. A pharmaceutical composition according to claim 32, which further comprises at least one second component selected from the group consisting of a beta$_2$-agonist, a corticosteroid, an anticholinergic agent, an antimuscarinic agent, and mixtures thereof.

35. A method of treating a disease of the respiratory tract characterized by airway obstruction, which comprises administering to a subject in need thereof a therapeutically effective amount of a compound according to claim 1, a pharmaceutically acceptable salt thereof, or a pyridine ring N-oxide thereof.

36. The method of claim 35, wherein said disease is selected from the group consisting of asthma or chronic bronchitis or chronic obstructive pulmonary disease (COPD).

37. A device, comprising a pharmaceutical composition according to claim 28.

38. The device according to claim 37, which is a single- or multi-dose dry powder inhaler.

39. The device according to claim 37, which is a metered dose inhaler.

40. The device according to claim 37, which is a soft mist nebulizer.

41. A process for the preparation of a compound of formula (IIA) according to claim 7, comprising:

a) reducing an ethanone of formula (5):

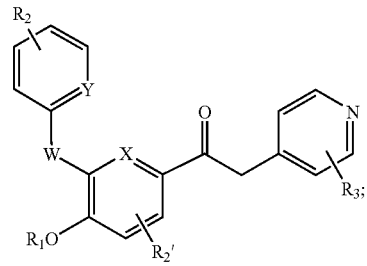

(5)

to give an alcohol compound of formula (6):

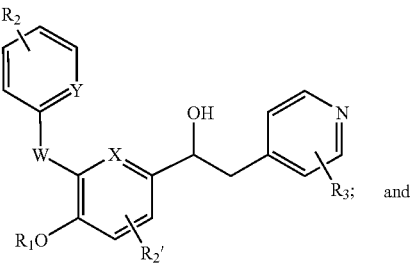

(6)

b) adding an acid of formula AZCOOH to a solution of said alcohol compound of formula (6), to obtain said compound of formula (IIA).

42. A process for the preparation of a compound of formula (IIB) according to claim 12, comprising:
  a) reacting an acyl chloride of formula (3) with a 4-methyl pyridine of formula (4) to give an ethanone of formula (5):

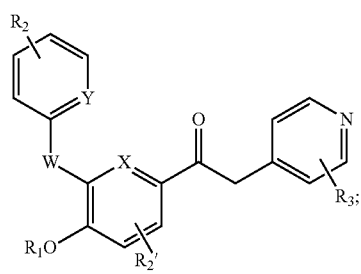

(5)

b) isolating said ethanone of formula (5);

c) reacting said ethanone with a strong base in an aprotic solvent, to obtain the corresponding enolate;

d) adding an acyl chloride of formula AZCOCl or an isocianate of formula ANCO or ACH$_2$NCO in a equimolar ratio or in a slight excess, wherein A and Z are as defined above.

* * * * *